United States Patent
Shoji et al.

(10) Patent No.: US 12,364,380 B2
(45) Date of Patent: Jul. 22, 2025

(54) INFORMATION PROCESSING APPARATUS, METHOD FOR CONTROLLING THE SAME, AND STORAGE MEDIUM STORING PROGRAM THEREFOR

(71) Applicant: CANON KABUSHIKI KAISHA, Tokyo (JP)

(72) Inventors: Takaaki Shoji, Tokyo (JP); Tomokazu Mori, Kanagawa (JP); Taro Matsuno, Tokyo (JP); Yoshihiko Okamoto, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 391 days.

(21) Appl. No.: 17/820,396

(22) Filed: Aug. 17, 2022

(65) Prior Publication Data

US 2023/0076864 A1 Mar. 9, 2023

(30) Foreign Application Priority Data

Sep. 9, 2021 (JP) .................. 2021-146854

(51) Int. Cl.
*A47L 11/40* (2006.01)
*A61L 2/24* (2006.01)
*G06F 3/16* (2006.01)
*G06V 40/16* (2022.01)
*G06V 40/20* (2022.01)

(52) U.S. Cl.
CPC ............. *A47L 11/4011* (2013.01); *A61L 2/24* (2013.01); *G06F 3/16* (2013.01); *G06V 40/171* (2022.01); *G06V 40/20* (2022.01); *A47L 2201/04* (2013.01); *A47L 2201/06* (2013.01); *A61L 2202/14* (2013.01); *A61L 2202/17* (2013.01); *A61L 2202/25* (2013.01)

(58) Field of Classification Search
CPC ............. A47L 2201/04; A47L 2201/06; A47L 11/4011; G06V 40/171; G06V 40/20; G06F 3/16; A61L 2/24; A61L 2202/14; A61L 2202/17; A61L 2202/25
See application file for complete search history.

(56) References Cited

U.S. PATENT DOCUMENTS 11,416,002 B1 * 8/2022 Day .................. G08B 13/19621

FOREIGN PATENT DOCUMENTS

JP       2013176471 A     9/2013

* cited by examiner

*Primary Examiner* — Andrew A Horton
(74) *Attorney, Agent, or Firm* — Canon U.S.A., Inc. IP Division

(57) ABSTRACT

An information processing apparatus includes a sound information generation unit configured to generate sound information in which a physiological sound of a body is extracted from an acquired sound, a sound direction detection unit configured to detect a direction of the physiological sound of the body based on the sound information, a facial state detection unit configured to detect a state of a face existing in the direction of the physiological sound of the body detected by the sound direction detection unit, from an image captured and generated by an imaging unit, and a contamination information generation unit configured to generate contamination information in which a predetermined area according to the state of the face is set as a contaminated area, based on the state of the face detected by the facial state detection unit.

22 Claims, 29 Drawing Sheets

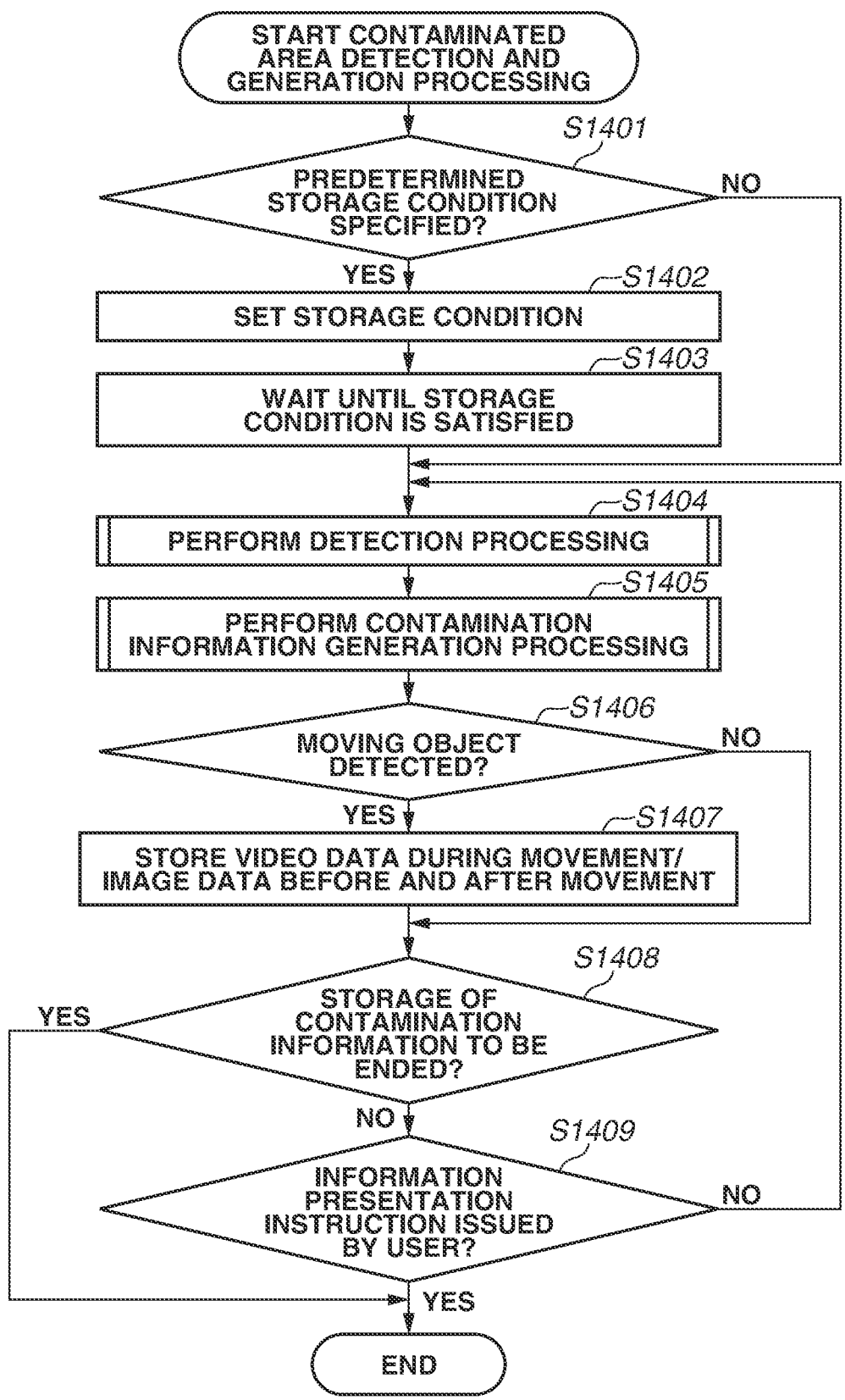

FIG.21A

| SUBJECT | TEMPERATURE [°C] | MEDICAL CONDITIONS | CONTAMINATION INFORMATION |
|---|---|---|---|
| SUBJECT A | 36.6 | SPRAIN | CONTAMINATED AREA A |
| SUBJECT B | 37.1 | COLD | CONTAMINATED AREA B |
| SUBJECT C | 38.9 | DESIGNATED INFECTION | CONTAMINATED AREA C |
| SUBJECT D | 35.9 | NONE | NONE |

FIG.21B

| SUBJECT | TEMPERATURE [°C] | MEDICAL CONDITIONS | CONTAMINATION INFORMATION | PRIORITY |
|---|---|---|---|---|
| SUBJECT A | 36.6 | SPRAIN | CONTAMINATED AREA A | LOW |
| SUBJECT B | 37.1 | COLD | CONTAMINATED AREA B | MIDDLE |
| SUBJECT C | 38.9 | DESIGNATED INFECTION | CONTAMINATED AREA C | HIGH |
| SUBJECT D | 35.9 | NONE | NONE | NONE |

FIG.21C

| SUBJECT | TEMPERATURE [°C] | MEDICAL CONDITIONS | CONTAMINATION INFORMATION | PRIORITY | CLEANING OPERATION | CLEANING RESULT DETERMINATION |
|---|---|---|---|---|---|---|
| SUBJECT A | 36.6 | SPRAIN | CONTAMINATED AREA A | LOW | CLEANING AGENT SPRAYING | OK |
| SUBJECT B | 37.1 | COLD | CONTAMINATED AREA B | MIDDLE | ULTRAVIOLET IRRADIATION | OK |
| SUBJECT C | 38.9 | DESIGNATED INFECTION | CONTAMINATED AREA C | HIGH | CLEANING AGENT SPRAYING & ULTRAVIOLET IRRADIATION | OK |
| SUBJECT D | 35.9 | NONE | NONE | NONE | NONE | NONE |

FIG.21D

| SUBJECT | TEMPERATURE [°C] | MEDICAL CONDITIONS | CONTAMINATION INFORMATION | PRIORITY | CLEANING OPERATION | CLEANING RESULT DETERMINATION |
|---|---|---|---|---|---|---|
| SUBJECT A | 36.6 | SPRAIN | CONTAMINATED AREA A | LOW | CLEANING AGENT SPRAYING | OK |
| SUBJECT B | 39.2 | DESIGNATED INFECTION | CONTAMINATED AREA B | HIGH | ULTRAVIOLET IRRADIATION | NG (MANUAL CLEANING REQUIRED) |
| SUBJECT C | 38.9 | DESIGNATED INFECTION | CONTAMINATED AREA C | HIGH | CLEANING AGENT SPRAYING & ULTRAVIOLET IRRADIATION | OK |
| SUBJECT D | 35.9 | NONE | NONE | NONE | NONE | NONE |

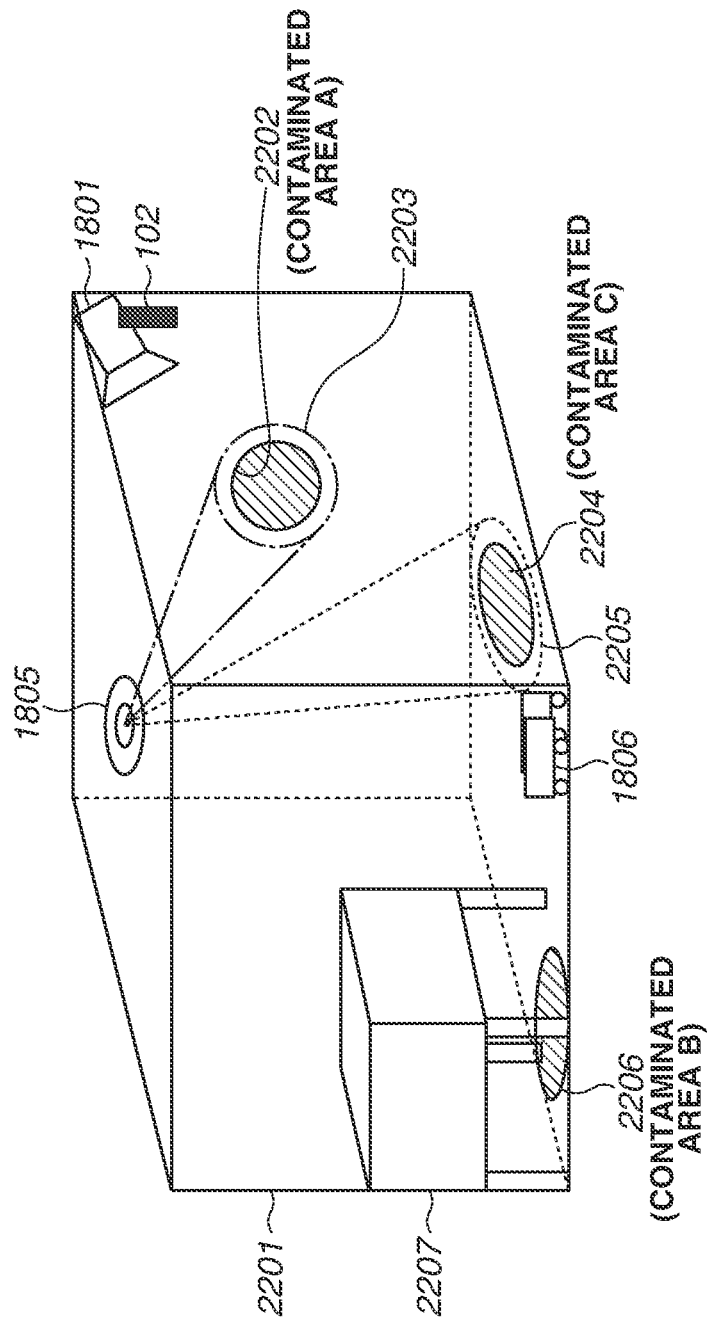

INFORMATION PROCESSING APPARATUS, METHOD FOR CONTROLLING THE SAME, AND STORAGE MEDIUM STORING PROGRAM THEREFOR

BACKGROUND

Field of the Disclosure

The present disclosure relates to an information processing apparatus, a method for controlling the information processing apparatus, and a storage medium storing a program for the control method.

Description of the Related Art

In recent years, diverse techniques for preventing the spread of infections have been proposed. Japanese Patent Application Laid-Open No. 2013-176471 proposes a technique for capturing in the direction of a sound source, measuring the body temperature of a person by using an infrared camera or collecting information about the mask wearing state to generate physical condition information for a group of people, and performing processing of preventing an infection epidemic.

An infection may be spread when droplets containing pathogens are scattered by an utterance, sneeze, or cough of a person, or another person touches a contaminated area with droplets. To prevent such an epidemic, it is effective to clean areas contaminated with droplets.

SUMMARY

The present disclosure has been devised in view of the above-described situation and is directed to identifying contaminated areas to which droplets scattered from persons adhere, and easily recognizing the contaminated areas to be cleaned.

An information processing apparatus includes a sound information generation unit configured to generate sound information in which a physiological sound of a body is extracted from an acquired sound, a sound direction detection unit configured to detect a direction of the physiological sound of the body based on the sound information, a facial state detection unit configured to detect a state of a face existing in the direction of the physiological sound of the body detected by the sound direction detection unit, from an image captured and generated by an imaging unit, and a contamination information generation unit configured to generate contamination information in which a predetermined area according to the state of the face is set as a contaminated area, based on the state of the face detected by the facial state detection unit.

Further features of various embodiments will become apparent from the following description of exemplary embodiments with reference to the attached drawings.

BRIEF DESCRIPTION OF THE DRAWINGS

FIG. 14 is a flowchart illustrating an example of contaminated area detection and generation processing according to a fourth exemplary embodiment.

FIGS. 21A to 21D illustrate examples of stored data, priority data, and cleaning result determination data in a data acquisition unit.

FIG. 22 illustrates a cleaning operation according to the sixth exemplary embodiment.

DESCRIPTION OF THE EMBODIMENTS

Exemplary embodiments will now be described with reference to the accompanying drawings.

Figure 1:
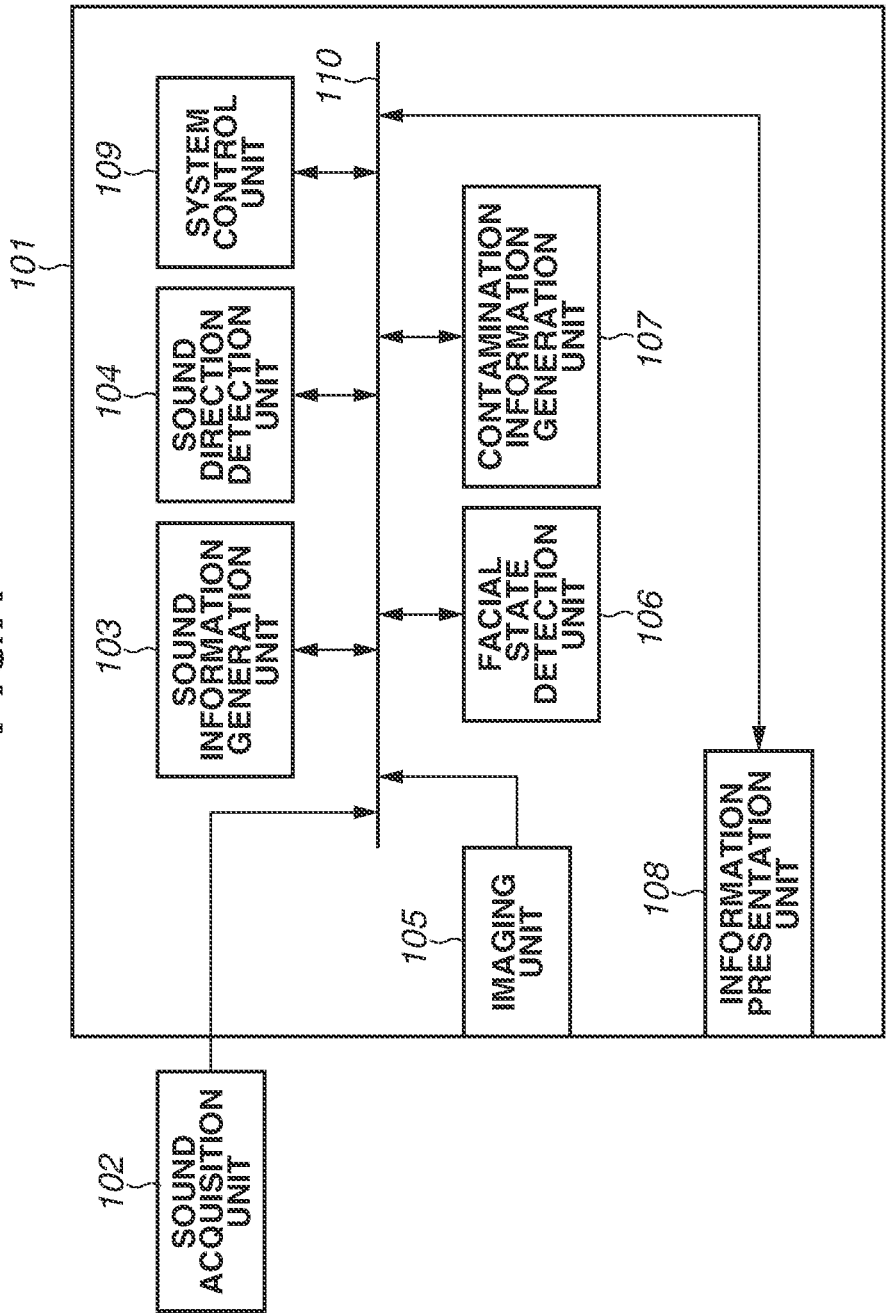
FIG. 1 illustrates an example configuration of an information processing apparatus according to a first exemplary embodiment.

FIG. 1 is a block diagram illustrating an example configuration of an information processing apparatus 101 according to a first exemplary embodiment. The information processing apparatus 101 includes a sound acquisition unit 102, a sound information generation unit 103, a sound direction detection unit 104, an imaging unit 105, a facial state detection unit 106, a contamination information generation unit 107, an information presentation unit 108, a system control unit 109, and a communication bus 110. The sound acquisition unit 102, the sound information generation unit 103, the sound direction detection unit 104, the imaging unit 105, the facial state detection unit 106, the contamination information generation unit 107, the information presentation unit 108, and the system control unit 109 are communicably connected with each other via the communication bus 110.

The sound acquisition unit 102 includes, for example, a plurality of microphones to acquire a sound.

The sound information generation unit 103 generates sound information in which a physiological sound of the body is extracted from the sound acquired by the sound acquisition unit 102. Examples of the physiological sound of the body include sounds generated by actions, such as an utterance, sneeze, cough, blow, and exhalation. For example, the sound information generation unit 103 stores patterns of physiological sounds of the body, performs pattern matching with sounds acquired by the sound acquisition unit 102, and extracts a physiological sound of the body. The sound information generation unit 103 extracts a physiological sound of the body for each microphone included in the sound acquisition unit 102. The sound information generation unit 103 also generates sound volume information indicating the sound volume of the physiological sound of the body.

The sound direction detection unit 104 detects a sound direction based on the sound information generated by the sound information generation unit 103. The sound direction detection unit 104 detects a direction of the physiological sound of the body, for example, based on the positions of the plurality of microphones composing the sound acquisition unit 102 and time differences between physiological sounds of the body extracted by the sound information generation unit 103 for each microphone The imaging unit 105 captures a subject to generate an image of the subject. The imaging unit 105 is, for example, an image sensor such as a charge coupled device (CCD) image sensor and a complementary metal oxide semiconductor (CMOS) image sensor. Although, in the example illustrated in FIG. 1, the imaging unit 105 is provided in the information processing apparatus 101, an apparatus having the function of the imaging unit 105 may be installed outside the information processing apparatus 101 to provide the information processing apparatus 101 with captured images.

The facial state detection unit 106 detects a face existing in the direction of the sound detected by the sound direction detection unit 104 to detect the facial state based on the image generated by the imaging unit 105. Examples of the facial state include a face orientation, a mask wearing state, and a distance between the imaging unit 105 and the face. The facial state detection unit 106 detects the face orientation based on, for example, a layout of facial feature points, such as eyes, nose, and mouth in the detected face. The facial state detection unit 106 also detects a mask wearing state, for example, according to whether the nose and mouth can be detected out of facial feature points such as the eyes, nose, and mouth in the detected face. The facial state detection unit 106 also detects, for example, a distance between the imaging unit 105 and the face depending on the distances between facial feature points, such as the eyes, nose, and mouth, in the detected face.

The contamination information generation unit 107 generates contamination information based on the facial state detected by the facial state detection unit 106. The contamination information indicates a predetermined area according to the facial state as a contaminated area to which scattered droplets adhere. The contamination information includes information that enables identifying a contaminated area, such as a distance, direction, and shape of the contamination. The distance of the contamination refers to the distance from the face (scattering source) to the area where scattered droplets reach, and the direction of the contamination refers to the direction in which droplets are scattered. The contamination information also includes the position of a contaminated area based on the distance between the imaging unit 105 and the face detected by the facial state detection unit 106 and the direction of the sound detected by the sound direction detection unit 104.

If the detected face wears a mask, the contamination information generation unit 107 shortens the distance of the contamination included in the contamination information, sets the direction of the contamination to the direction of the leakage from the gap between the mask and the face, and sets the shape of the contamination to the shape of the leakage from the gap between the mask and the face. The contamination information generation unit 107 also changes the contamination information to increase the distance of the contamination or the shape size of the contamination with increasing sound volume based on the sound volume information generated by the sound information generation unit 103.

The contamination information generation unit 107 also stores contamination information satisfying a predetermined storage condition and combines pieces of the stored contamination information to generate combined contamination information. The predetermined storage condition refers to the fact that, for example, the contamination information is generated in the time period when an instruction is issued from the user via the information presentation unit 108 or the time period since the sound acquisition unit 102 starts the sound acquisition until an instruction for presenting the combined contamination information is issued by the user. The contamination information generation unit 107 also deletes the contamination information satisfying a predetermined deletion condition out of the stored contamination information. The predetermined deletion condition refers to the fact that, for example, the time period when the contamination information is generated is included in the time period when an instruction is issued from the user via the information presentation unit 108 or the time period since the sound acquisition unit 102 starts the sound acquisition until an instruction for presenting the combined contamination information is issued by the user.

The information presentation unit 108 includes, for example, a display member, such as a monitor having a touch panel function. The information presentation unit 108 converts the contamination information or the combined contamination information as required and then presents the information, upon reception of, for example, an instruction from the user. The information presentation unit 108 converts the information about the distance, direction, shape, and position of the contamination included in the contamination information or the combined contamination information into information that enables the user to recognize a contaminated area, such as a sound and a video. Examples of instructions received by the information presentation unit 108 issued by the user include, for example, an instruction for starting the presentation of the contamination information or the combined contamination information, an instruction for ending the presentation thereof, an instruction for the time period during which the contamination information is stored, and an instruction for the time period during which the contamination information is deleted.

The system control unit 109 controls the entire information processing apparatus 101 via the communication bus 110. The system control unit 109 implements each piece of processing (described below) by executing a program recorded in a storage unit, such as a nonvolatile memory (not illustrated).

The communication bus 110 connects the function units configuring the information processing apparatus 101 with each other.

Figure 2:
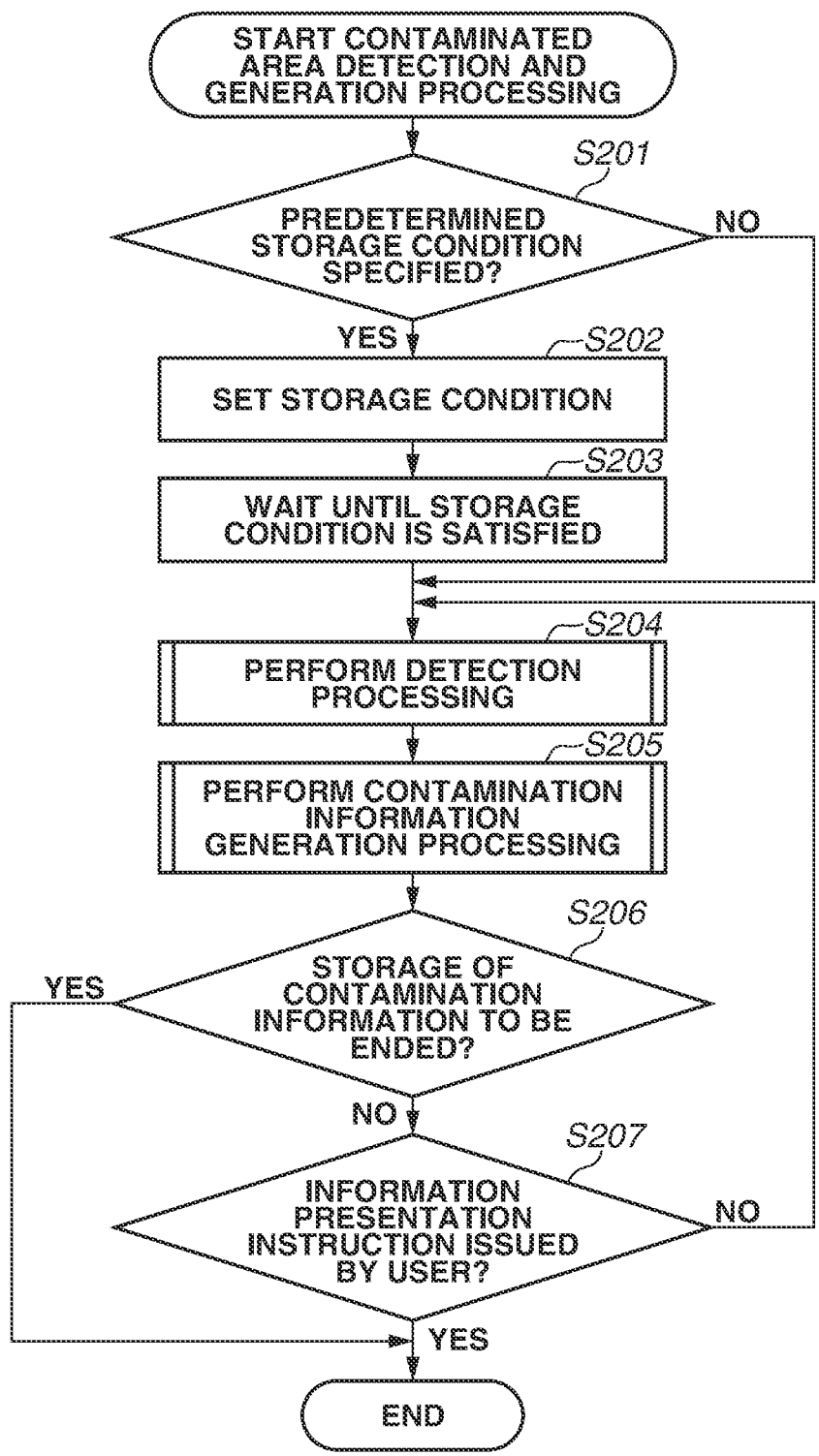
FIG. 2 is a flowchart illustrating an example of contaminated area detection and generation processing according to the first exemplary embodiment.

The contaminated area detection and generation processing performed by the information processing apparatus 101 will now be described with reference to FIG. 2. FIG. 2 is a flowchart illustrating an example of the contaminated area detection and generation processing according to the first exemplary embodiment. The information processing apparatus 101 starts the contaminated area detection and generation processing illustrated in FIG. 2 when, for example, power of the apparatus is turned ON. The information processing apparatus 101 may also start the contaminated area detection and generation processing illustrated in FIG. 2 upon reception of an instruction from the user.

In step S201, the system control unit 109 determines whether the predetermined storage condition is specified via the information presentation unit 108. The predetermined storage condition to be specified refers to, for example, the time period during which the contamination information is stored. When the system control unit 109 determines that the predetermined storage condition is specified (YES in step S201), the processing proceeds to step S202. In contrast, when the system control unit 109 determines that the predetermined storage condition is not specified (NO in step S201), the processing proceeds to step S204.

In step S202, the system control unit 109 sets the predetermined storage condition. Upon completion of the storage condition setting, the processing proceeds to step S203.

In step S203, the system control unit 109 waits until the predetermined storage condition set in step S202 is satisfied. When the predetermined storage condition set in step S202 is satisfied, the processing proceeds to step S204.

In step S204, the system control unit 109 controls the sound acquisition unit 102, the sound information generation unit 103, the sound direction detection unit 104, and the facial state detection unit 106 to perform detection processing. The detection processing in step S204 will be described in detail below with reference to FIG. 3. Upon completion of the detection processing, the processing proceeds to step S205.

In step S205, referring to the result of the detection processing performed in step S204, the system control unit 109 controls the contamination information generation unit 107 to perform the contamination information generation processing. The contamination information generation processing in step S205 will be described in detail below with reference to FIG. 4. Upon completion of the contamination information generation processing, the processing proceeds to step S206.

In step S206, the system control unit 109 checks whether a condition for ending the storage of the contamination information is set in the predetermined storage condition and determines whether to end the storage of the contamination information. The condition for ending the storage of the contamination information refers to, for example, the fact that the time period during which the contamination information is stored has ended. When the system control unit 109 determines that the condition for ending the storage of the contamination information is satisfied and determines to end the storage of the contamination information (YES in step S206), the system control unit 109 completes the contaminated area detection and generation processing. In contrast, when the system control unit 109 determines that the condition for ending the storage of the contamination information is not satisfied and determines not to end the storage of the contamination information (NO in step S206), the processing proceeds to step S207.

In step S207, the system control unit 109 determines whether an information presentation instruction for requesting to present the contamination information or the combined contamination information is issued from the user via the information presentation unit 108.

When the system control unit 109 determines that the information presentation instruction is issued (YES in step S207), the system control unit 109 completes the contaminated area detection and generation processing. In contrast, when the system control unit 109 determines that no information presentation instruction is issued (NO in step S207), the processing returns to step S204.

Figure 3:
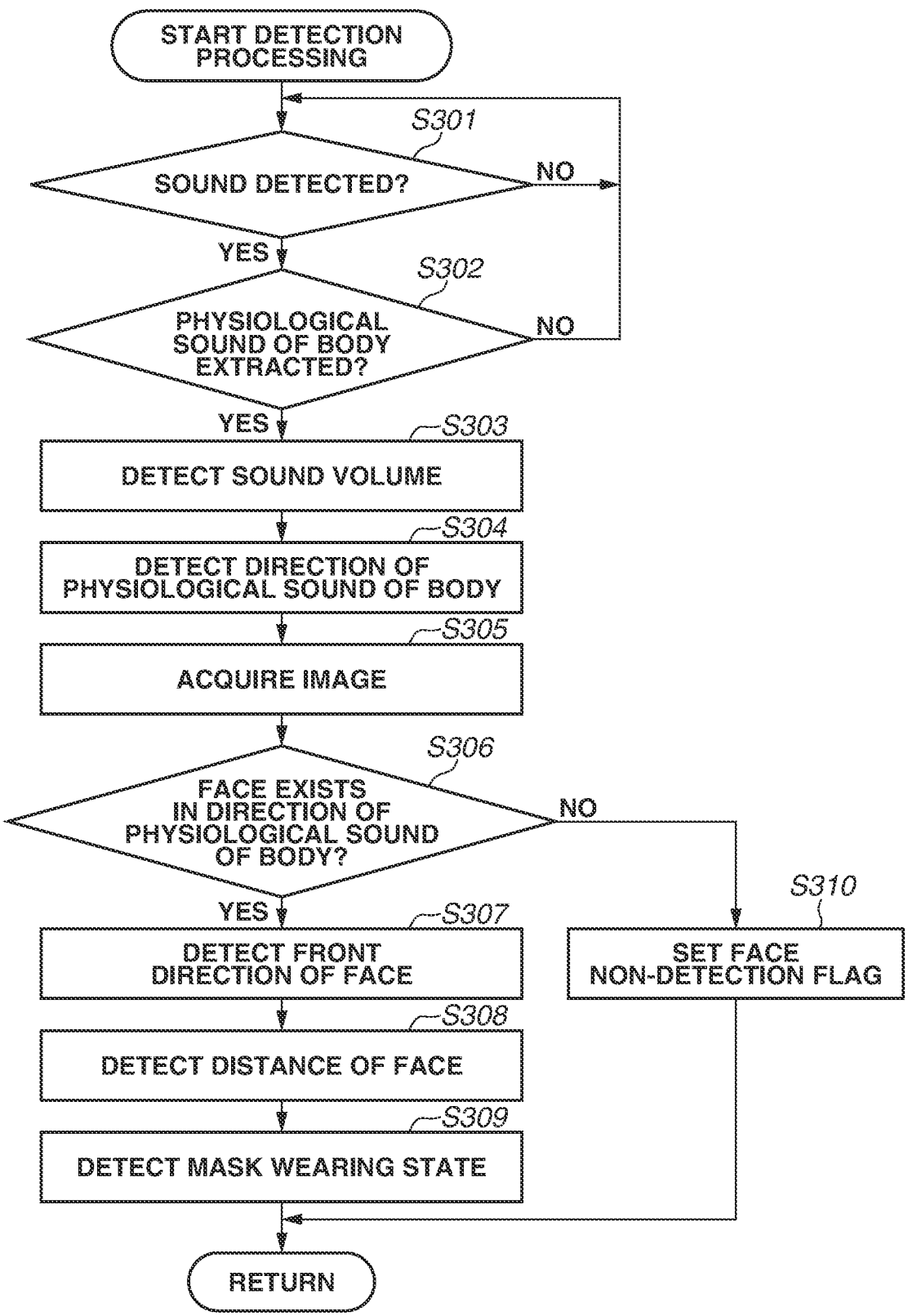
FIG. 3 is a flowchart illustrating an example of detection processing according to the first exemplary embodiment.

The detection processing in step S204 in FIG. 2 will now be described with reference to FIG. 3. FIG. 3 is a flowchart illustrating an example of the detection processing. The processing of the flowchart illustrated in FIG. 3 is implemented when the system control unit 109 controls each function unit.

In step S301, the sound acquisition unit 102 determines whether a sound is acquired. When the sound acquisition unit 102 determines that no sound is acquired (NO in step S301), the sound acquisition unit 102 repeats step S301 until a sound is acquired. When the sound acquisition unit 102 determines that a sound is acquired (YES in step S301), the processing proceeds to step S302.

In step S302, the sound information generation unit 103 determines whether a physiological sound of the body can be extracted from the sound acquired by the sound acquisition unit 102 in step S301. When the sound information generation unit 103 determines that a physiological sound of the body can be acquired (YES in step S302), the sound information generation unit 103 generates sound information in which a physiological sound of the body is extracted. The processing then proceeds to step S303. When the sound information generation unit 103 determines that no physiology sound of the body can be acquired (NO in step S302), the processing returns to step S301.

In step S303, the sound information generation unit 103 generates sound volume information indicating the sound volume of the physiological sound of the body extracted in step S302. Upon completion of the sound volume information generation, the processing proceeds to step S304.

In step S304, the sound direction detection unit 104 detects the direction of the physiological sound of the body extracted in step S302. Upon completion of detecting the sound direction, the processing proceeds to step S305.

In step S305, the imaging unit 105 captures an image of a subject. Upon completion of acquiring the captured image, the processing proceeds to step S306.

In step S306, the facial state detection unit 106 determines whether a face exists in the direction of the sound detected by the sound direction detection unit 104 in step S304 based on the image acquired in step S305. When the facial state detection unit 106 determines that a face exist in the direction of the detected sound (YES in step S306), the processing proceeds to step S307. When the facial state detection unit 106 determines that no face exists in the direction of the detected sound (NO in step S306), the processing proceeds to step S310.

In step S307, the facial state detection unit 106 detects the front direction of the face existing in the direction of the physiological sound of the body detected in step S304. Upon completion of the detection of the front direction of the face, the processing proceeds to step S308.

In step S308, the facial state detection unit 106 detects the distance between the face existing in the direction of the physiological sound of the body detected in step S304 and the imaging unit 105. Upon completion of the detection of the distance between the face and the imaging unit 105, the processing proceeds to step S309.

In step S309, the facial state detection unit 106 detects the mask wearing state of the face existing in the direction of the physiological sound of the body detected in step S304. Upon completion of the detection of the mask wearing state, the facial state detection unit 106 completes the detection processing. Then, the processing proceeds to step S205 in FIG. 2.

The execution order of the processing in steps S307, S308, and S309 is not limited to the example illustrated in FIG. 3 but may be in another (e.g., a random) order.

In step S310, the facial state detection unit 106 sets a face non-detection flag. Upon completion of the face non-detection flag setting, the facial state detection unit 106 completes the detection processing. Then, the processing proceeds to step S205 in FIG. 2.

Figure 4:
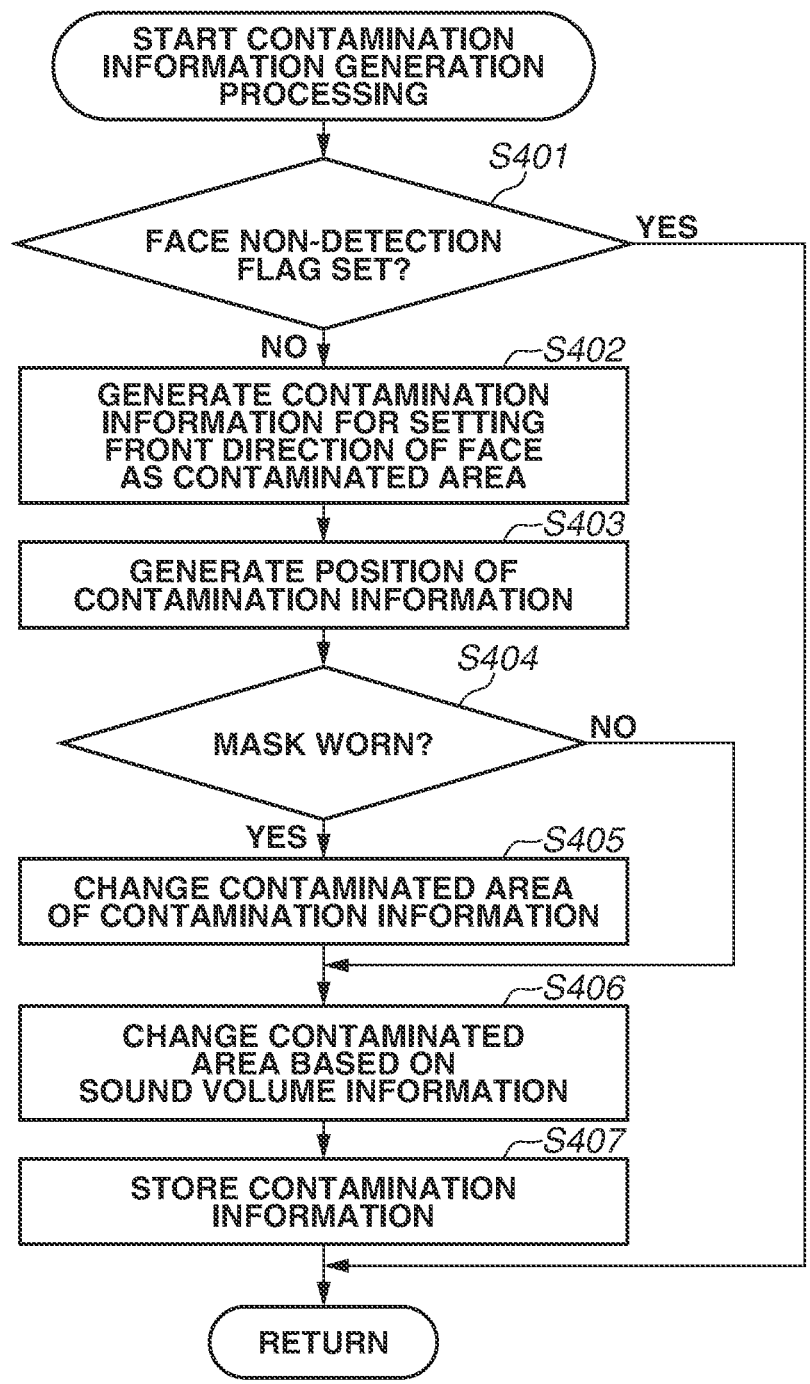
FIG. 4 is a flowchart illustrating an example of contamination information generation processing according to the first exemplary embodiment.

The contamination information generation processing in step S205 in FIG. 2 will now be described with reference to FIG. 4. FIG. 4 is a flowchart illustrating an example of the contamination information generation processing. The processing of the flowchart illustrated in FIG. 4 is implemented when the system control unit 109 controls each function unit.

In step S401, the contamination information generation unit 107 determines whether the face non-detection flag is set in step S310 in FIG. 3. When the contamination information generation unit 107 determines that the face non-detection flag is set (YES in step S401), the contamination information generation unit 107 completes the contamination information generation processing without generating the contamination information. Then, the processing proceeds to step S206 in FIG. 2. In contrast, when the contamination information generation unit 107 determines that the face non-detection flag is not set (NO in step S401), the processing proceeds to step S402.

In step S402, the contamination information generation unit 107 generates the contamination information in which a predetermined area in the front direction of the face detected in step S307 in FIG. 3 is set as a contaminated area to which droplets adhere. Upon completion of the contamination information generation, the processing proceeds to step S403.

In step S403, the contamination information generation unit 107 generates a position of the contaminated area based on the direction of the physiological sound of the body detected in step S304 in FIG. 3 and the distance between the face and the imaging unit 105 detected in step S308 in FIG. 3. Upon completion of the inclusion of the generated position of the contaminated area in the contamination information, the processing proceeds to step S404.

In step S404, the contamination information generation unit 107 determines whether the face wears a mask based on the mask wearing state detected in step S309 in FIG. 3. When the contamination information generation unit 107 determines that the face wears a mask (YES in step S404), the processing proceeds to step S405. In contrast, when the contamination information generation unit 107 determines that the face does not wear a mask (NO in step S404), the processing proceeds to step S406.

In step S405, the contamination information generation unit 107 changes the contaminated area of the contamination information generated in step S402. Examples of changes made in step S405 include decreasing the distance of the contamination included in the contamination information, setting the direction of the contamination to the direction of the leakage from the gap between the mask and the face, and setting the shape of the contamination to the shape of the leakage from the gap between the mask and the face. Upon completion of the contamination information change in step S405, the processing proceeds to step S406.

In step S406, the contamination information generation unit 107 changes the contaminated area of the contamination information generated in step S402 or the contaminated area of the contamination information changed in step S405 based on the sound volume information generated in step S303 in FIG. 3. Examples of changes made in step S406 include increasing the distance of the contamination information or enlarging the shape of the contamination information with increasing sound volume. The changes made in step S406 may be performed based on the positions of the plurality of microphones included in the sound acquisition unit 102 and the relative position of the contaminated area generated in step S403. For example, with a large relative position and a large sound volume, the distance of the contamination information or the shape of the contamination information may be increased. Upon completion of the contamination information change in step S406, the processing proceeds to step S407.

In step S407, the contamination information generation unit 107 stores the contamination information. Upon completion of the contamination information storage, the contamination information generation unit 107 completes the contamination information generation processing. Then, the processing proceeds to step S206 in FIG. 2.

Figure 5:
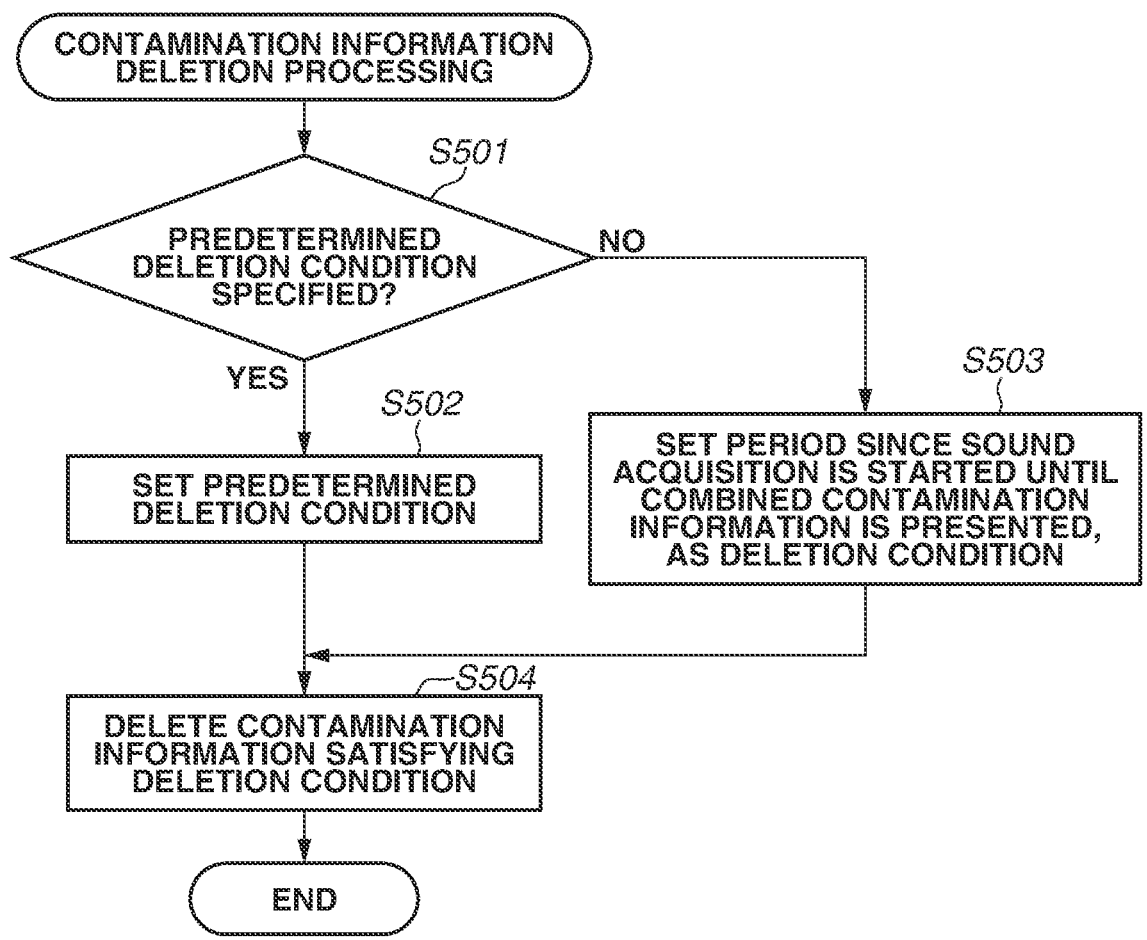
FIG. 5 is a flowchart illustrating an example of contamination information generation processing according to the first exemplary embodiment.

The contamination information deletion processing performed by the information processing apparatus 101 will now be described with reference to FIG. 5. FIG. 5 is a flowchart illustrating an example of the contamination information deletion processing. The processing of the flowchart illustrated in FIG. 5 is implemented when the system control unit 109 controls each function unit. The contamination information deletion processing in FIG. 5 is performed, for example, after completion of the contamination information presentation processing described below with reference to FIG. 6.

In step S501, the system control unit 109 determines whether a predetermined deletion condition is specified via the information presentation unit 108. The specified predetermined deletion condition refers to, for example, the time period during which the contamination information is deleted. When the system control unit 109 determines that the predetermined deletion condition is specified (YES in step S501), the processing proceeds to step S502. When the system control unit 109 determines that the predetermined deletion condition is not specified (NO in step S501), the processing proceeds to step S503.

In step S502, the system control unit 109 sets the specified predetermined deletion condition. Upon completion of the deletion condition setting in step S502, the processing proceeds to step S504.

In step S503, the system control unit 109 sets the time period since the sound acquisition is started until the combined contamination information is presented, as the deletion condition. Upon completion of the deletion condition setting in step S503, the processing proceeds to step S504.

In step S504, the contamination information generation unit 107 deletes the contamination information satisfying the deletion condition set in step S502 or S503. Upon completion of the deletion of the contamination information satisfying the deletion condition, the system control unit 109 completes the contamination information deletion processing.

Figure 6:
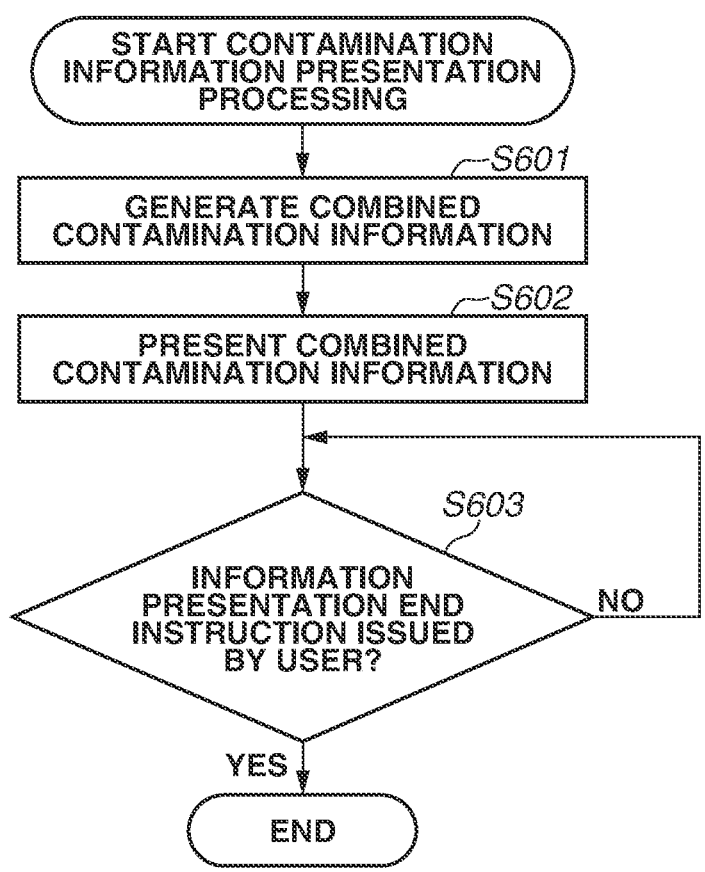
FIG. 6 is a flowchart illustrating an example of contamination information generation processing according to the first exemplary embodiment.

The contamination information presentation processing performed by the information processing apparatus 101 will now be described with reference to FIG. 6. FIG. 6 is a flowchart illustrating an example of the contamination information presentation processing. The processing of the flowchart illustrated in FIG. 6 is implemented when the system control unit 109 controls each function unit. The contamination information presentation processing in FIG. 6 is performed after completion of the contaminated area detection and generation processing described above with reference to FIG. 2.

In step S601, the contamination information generation unit 107 combines pieces of the stored contamination information to generate the combined contamination information. Upon completion of the combined contamination information generation, the processing proceeds to step S602.

In step S602, the information presentation unit 108 converts the combined contamination information generated in step S601 and then presents the information. The information presentation unit 108 converts the information about the distance, direction, shape, and position of the contamination included in the combined contamination information into a user-recognizable image, and displays the image, thereby presenting the combined contamination information. Upon completion of the combined contamination information presentation, the processing proceeds to step S603.

In step S603, the information presentation unit 108 determines whether an information presentation end instruction for requesting to end the presentation of the combined contamination information is issued by the user. When the information presentation unit 108 determines that no information presentation end instruction is issued (NO in step S603), the information presentation unit 108 continues the presentation of the information, and the processing proceeds to step S603. In contrast, when the information presentation unit 108 determines that the information presentation end instruction is issued (YES in step S603), the information processing apparatus 101 completes the contamination information presentation processing.

Figure 7:
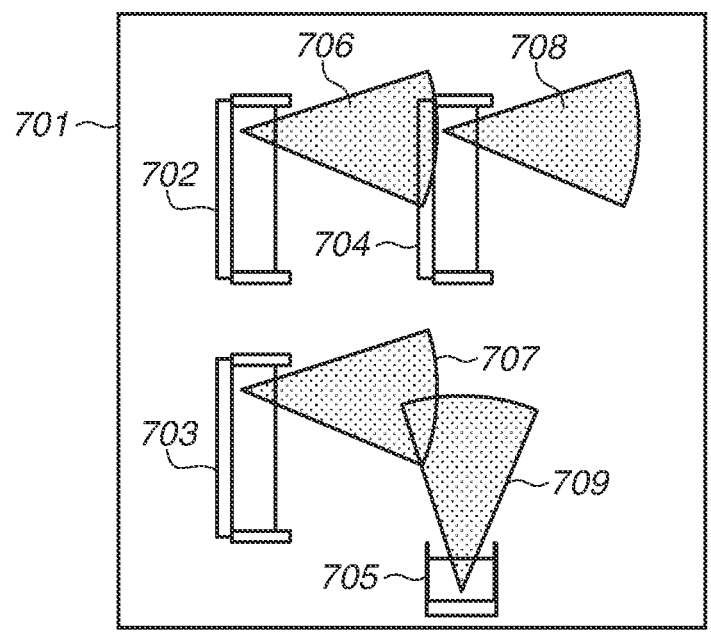
FIG. 7 illustrates an example of contamination information presentation according to the first exemplary embodiment.

FIG. 7 illustrates an example of the combined contamination information presented by the information processing apparatus 101. The example illustrated in FIG. 7 is the combined contamination information generated by the information processing apparatus 101 installed on the ceiling of a room 701. In the room 701, chairs 702, 703, 704, and 705 are installed. As contaminated areas to which scattered droplets adhere, FIG. 7 illustrates areas 706, 707, 708, and 709, which correspond to pieces of the stored contamination information. These areas are presented as the combined contamination information as a result of combining pieces of the contamination information. The vertex of each of the areas 706 to 709 (center of a fan shape) is a face position, which is indicating that the front directions of the faces of the persons sitting on the chairs 702 to 705 are contaminated.

According to the first exemplary embodiment, the information processing apparatus 101 extracts a physiological sound of the body from the sound acquired by the sound acquisition unit 102, detects the state of the face existing in the direction of the physiological sound of the body, generates contaminated area information in which a predetermined area according to the facial state is set as a contaminated area, and presents the information. By detecting and presenting a contaminated area based on the direction of the physiological sound of the body, such as the sound of an utterance, sneeze, cough, blow, and exhalation, and the facial state in this way, it becomes possible to recognize a contaminated area to which droplets scattered from a person adhere. It is also possible to recognize a contaminated area to which droplets scattered from a person adhere, enabling efficient cleaning.

The information presentation unit 108 including, for example, operation buttons and a projector may receive an operation instruction from the user, convert the contamination information or the combined contamination information into an image, and project the image for presentation. The conversion of the contamination information or the combined contamination information performed by the information presentation unit 108 may include the conversion into mapping information in which a video is mapped on an object.

When the information presentation unit 108 maps a video on the object, the shape of the object may be extracted from, for example, the image captured by the imaging unit 105 or may be preregistered. In this case, in step S602 (contamination information presentation processing) in FIG. 6, the information presentation unit 108 needs to convert the video of the combined contamination information generated in step S601 into the mapping information in which a video is mapped on an object, and project the information for presentation.

By converting the contaminated area into a video and projecting the video to an object for presentation in this way, it becomes possible to visually recognize a contaminated area to which droplets scattered from a person adhere. It is also possible to visually recognize a contaminated area to which droplets scattered from a person adhere, enabling efficient cleaning.

Figure 8:
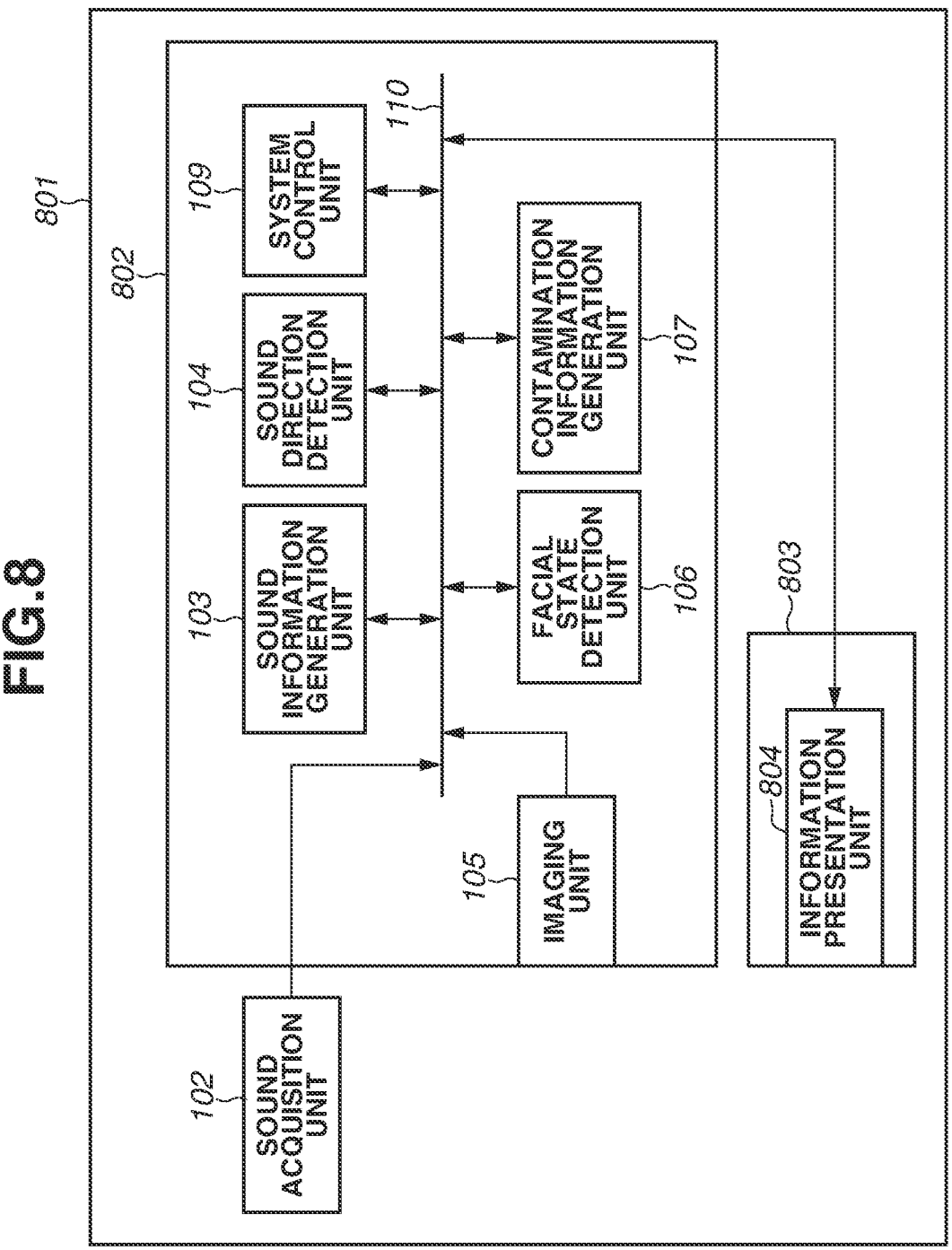
FIG. 8 illustrates an example of an information processing system according to a second exemplary embodiment.

FIG. 8 is a block diagram illustrating an example configuration of an information processing system 801 according to a second exemplary embodiment. Referring to FIG. 8, components having identical functions to those illustrated in FIG. 1 are assigned the same reference numerals and duplicated descriptions thereof will be omitted. An information processing system 801 includes an information processing apparatus 802 and an information presentation apparatus 803. The information processing apparatus 802 includes a sound acquisition unit 102, a sound information generation unit 103, a sound direction detection unit 104, an imaging unit 105, a facial state detection unit 106, a contamination information generation unit 107, a system control unit 109, and a communication bus 110. An information presentation apparatus 803 is, for example, augmented reality (AR) glasses. The information presentation apparatus 803 includes an information presentation unit 804.

The information presentation unit 804 includes, for example, operation buttons, a loud speaker, a transmissive monitor, a gyroscope sensor, and an acceleration sensor. Upon reception of an instruction from an operating user, for example, the information presentation unit 804 suitably converts the contamination information or the combined contamination information and displays the resultant information for presentation. The conversion of the contamination information or the combined contamination information performed by the information presentation unit 804 refers to, for example, the conversion into a sound and a video. The conversion of the contamination information or the combined contamination information performed by the information presentation unit 804 includes the conversion into mapping information in which a video is mapped on an object. The shape of the object when the information presentation unit 804 maps a video on an object may be, for example, extracted from the image captured by the imaging unit 105 or preregistered.

The information presentation unit 804 having a self-position estimation function can also generate self-position estimation information in which the position of the information presentation apparatus 803 is estimated. The information presentation apparatus 803 performs the self-position estimation, for example, by detecting the information presentation apparatus 803 from the image captured by the imaging unit 105 and calculating the self-position based on information from the gyroscope sensor and the acceleration sensor. Examples of instructions from the user received by the information presentation unit 804 include an instruction for starting the presentation of the contamination information or the combined contamination information, an instruction for ending the presentation thereof, an instruction for the time period during which the contamination information is stored, and an instruction for the time period during which the contamination information is deleted.

The contaminated area detection and generation processing performed by the information processing system 801 according to the second exemplary embodiment is similar to the contaminated area detection and generation processing according to the first exemplary embodiment described above with reference to FIGS. 2 to 4, and therefore descriptions thereof will be omitted. Also, the contamination information deletion processing performed by the information processing system 801 according to the second exemplary embodiment is similar to the contamination information deletion processing according to the first exemplary embodiment described above with reference to FIG. 5, and descriptions thereof will be omitted.

The contamination information presentation processing performed by the information processing system 801 will now be described with reference to FIG. 9.

Figure 9:
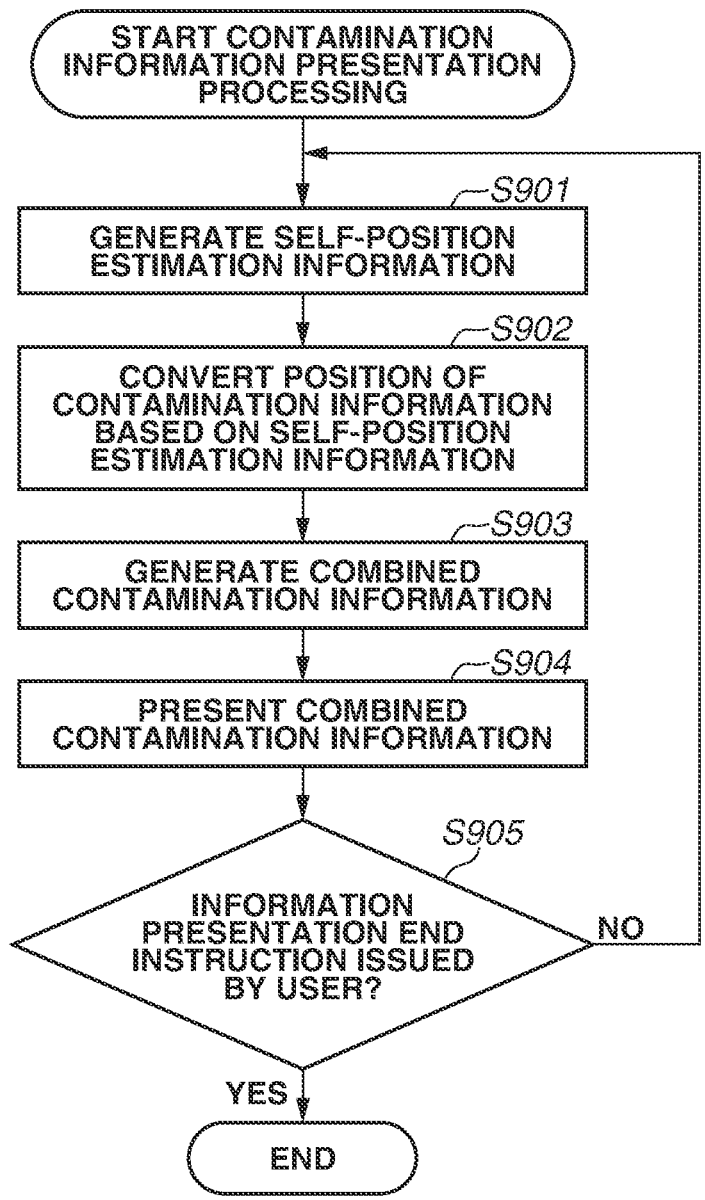
FIG. 9 is a flowchart illustrating an example of contamination information presentation processing according to the second exemplary embodiment.

FIG. 9 is a flowchart illustrating an example of the contamination information presentation processing. The processing of the flowchart illustrated in FIG. 9 is implemented when the system control unit 109 controls each function unit. The contamination information presentation processing in FIG. 9 is performed after completion of the contaminated area detection and generation processing described above with reference to FIG. 2.

In step S901, the information presentation unit 804 estimates the position of the information presentation apparatus 803 and generates the self-position estimation information.

In step S902, based on the self-position estimation information generated by the information presentation unit 804 in step S901, the information presentation unit 804 converts the information about the position of the contaminated area out of the contamination information stored by the contamination information generation unit 107 into a relative position that is relative to the self-position estimation information. Upon completion of the conversion of the position of the contaminated area in the contamination information into a relative position, the processing proceeds to step S903.

In step S903, the contamination information generation unit 107 combines pieces of the contamination information as a result of the conversion in step S902 to generate the combined contamination information. Upon completion of the combined contamination information generation, the processing proceeds to step S904.

In step S904, the information presentation unit 804 displays the combined contamination information generated in step S903 for presentation. The information presentation unit 804 may also output, from a speaker, a warning sound with a larger sound volume for a closer relative position for presentation, based on the relative position to the position of the contaminated area as a result of the conversion in step S902.

In step S905, the information presentation unit 804 determines whether an information presentation end instruction for requesting to end the presentation of the combined contamination information is issued by the user. When the information presentation unit 804 determines that no information presentation end instruction is issued (NO in step S905), the processing returns to step S901. When the information presentation unit 804 determines that the information presentation end instruction is issued (YES in step S905), the system control unit 109 completes the contamination information presentation processing. Upon completion of the contamination information presentation processing described above with reference to FIG. 9, the information processing system 801 performs the contamination information deletion processing described above with reference to FIG. 5.

According to the second exemplary embodiment, the information processing apparatus 802 extracts a physiological sound of the body from the sound acquired by the sound acquisition unit 102, detects the state of the face existing in the direction of the physiological sound of the body, and generates contaminated area information in which a predetermined area according to the facial state is set as a contaminated area. Then, based on the self-position estimation information generated by the information presentation unit 804, the information processing apparatus 802 presents the contaminated area in a form that makes it easier to perform estimation from the self-position of the user who wears the information presentation apparatus 803. This enables recognizing in detail the contaminated area to which droplets scattered from a person adhere, making it possible to efficiently clean the contaminated area.

Figure 10:
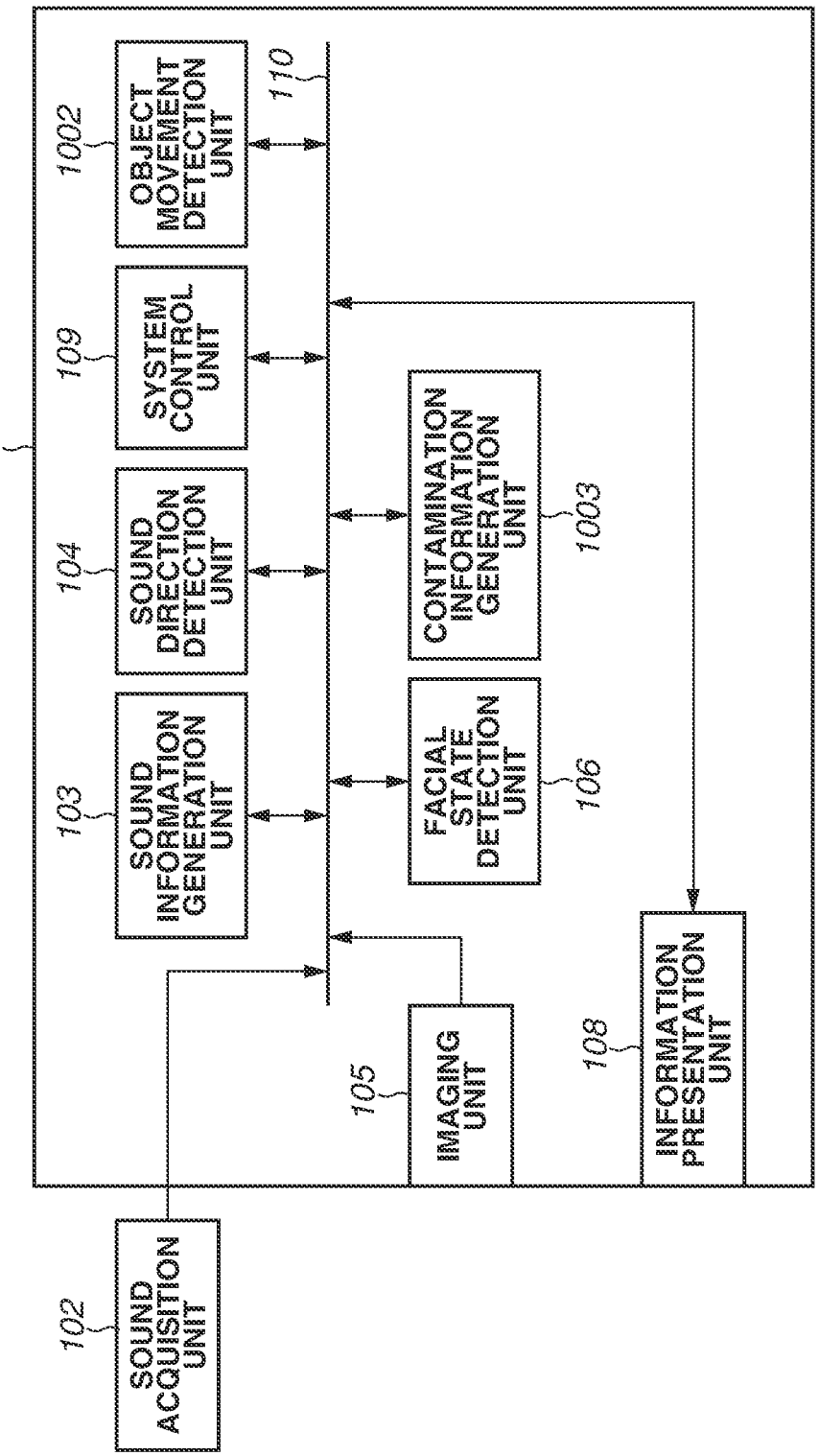
FIG. 10 illustrates an example configuration of an information processing apparatus according to a third exemplary embodiment.

In a third exemplary embodiment, the stored contamination information according to the movement of the object is updated when an object existing in a certain contaminated area is moved. FIG. 10 is a block diagram illustrating an example configuration of an information processing apparatus 1001 according to the third exemplary embodiment.

Referring to FIG. 10, components having identical functions to those illustrated in FIG. 1 are assigned the same reference numerals and duplicated descriptions thereof will be omitted. The information processing apparatus 1001 includes a sound acquisition unit 102, a sound information generation unit 103, a sound direction detection unit 104, an imaging unit 105, a facial state detection unit 106, an information presentation unit 108, a system control unit 109, a communication bus 110, an object movement detection unit 1002, and a contamination information generation unit 1003.

The object movement detection unit 1002 detects a moving object in an image captured by the imaging unit 105. The object movement detection unit 1002 detects the range where the detected moving object has existed before the movement and the range where the detected moving object exists after the movement, as movement information for the moving object. A known movement detection technique is used for the moving object detection by the object movement detection unit 1002. The technique analyzes a captured image and then performs pattern matching on an object and tracks the object by using a motion vector.

The contamination information generation unit 1003 generates contamination information in which a predetermined area according to the facial state is set as a contaminated area to which scattered droplets adhere based on the facial state detected by the facial state detection unit 106. The contamination information generation unit 1003 also updates the contents of the generated contamination information based on the movement information detected by the object movement detection unit 1002. The update of the movement information detected by the object movement detection unit 1002 and the contamination information generated by the contamination information generation unit 1003 will now be described in detail.

Figure 11:
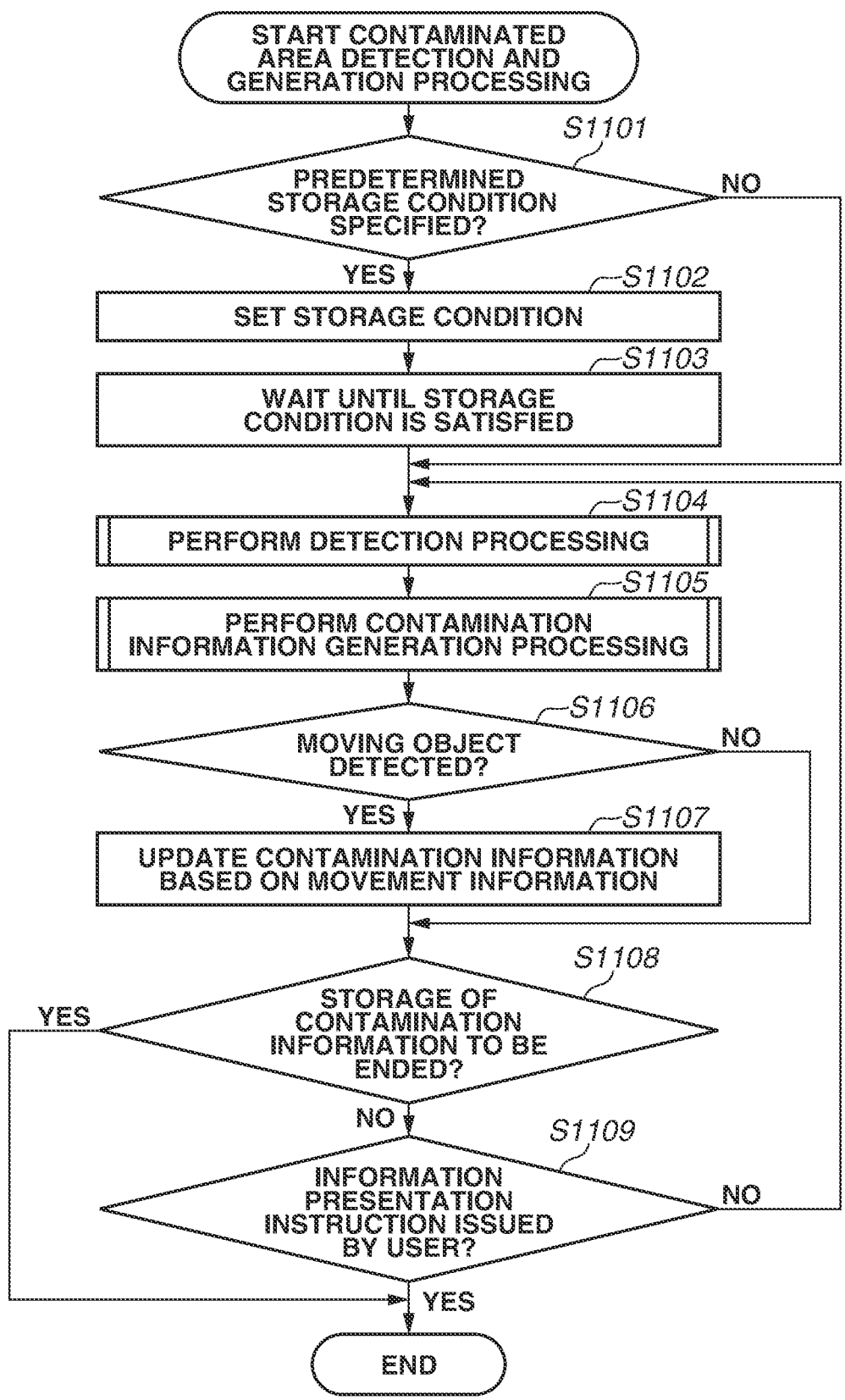
FIG. 11 is a flowchart illustrating an example of contaminated area detection and generation processing according to the third exemplary embodiment.

The contaminated area detection and generation processing performed by the information processing apparatus 1001 will now be described with reference to FIG. 11. FIG. 11 is a flowchart illustrating an example of the contaminated area detection and generation processing according to the third exemplary embodiment. The information processing apparatus 1001 starts the contaminated area detection and generation processing illustrated in FIG. 11, for example, when power of the apparatus is turned ON. The information processing apparatus 1001 may start the contaminated area detection and generation processing illustrated in FIG. 11 upon reception of an instruction from the user.

In step S1101, the system control unit 109 determines whether the predetermined storage condition is specified via the information presentation unit 108. The predetermined storage condition to be specified refers to, for example, the time period during which the contamination information is stored. When the system control unit 109 determines that the predetermined storage condition is specified (YES in step S1101), the processing proceeds to step S1102. In contrast, when the system control unit 109 determines that the predetermined storage condition is not specified (NO in step S1101), the processing proceeds to step S1104.

In step S1102, the system control unit 109 sets the predetermined storage condition. Upon completion of the storage condition setting, the processing proceeds to step S1103.

In step S1103, the system control unit 109 waits until the predetermined storage condition set in step S1102 is satisfied. When the predetermined storage condition is satisfied, the processing proceeds to step S1104.

In step S1104, the system control unit 109 controls the sound acquisition unit 102, the sound information generation unit 103, the sound direction detection unit 104, and the facial state detection unit 106 to perform the detection processing. The detection processing in step S1104 is similar in detail to the detection processing according to the first exemplary embodiment described above with reference to FIG. 3, and descriptions thereof will be omitted. Upon completion of the detection processing, the processing proceeds to step S1105.

In step S1105, referring to the result of the detection processing performed in step S1104, the system control unit 109 controls the contamination information generation unit 1003 to perform the contamination information generation processing. The contamination information generation processing in step S1105 is similar in detail to the contamination information generation processing according to the first exemplary embodiment described above with reference to FIG. 4, and thus descriptions thereof will be omitted. Upon completion of the contamination information generation processing, the processing proceeds to step S1106.

In step S1106, the system control unit 109 controls the object movement detection unit 1002 to perform the moving object detection processing and determines whether a moving object is detected in the image captured by the imaging unit 105. In the moving object detection processing, the object movement detection unit 1002 detects a moving object in the image captured by the imaging unit 105 and detects the area where the moving object has existed before the movement and the area where the moving object exists after the movement, as movement information for the moving object. The movement information for the detected moving object is transmitted to the contamination information generation unit 1003. As described above, a known movement detection technique may be used for the moving object detection by the object movement detection unit 1002.

When the system control unit 109 determines that a moving object is detected in the captured image (YES in step S1106), the processing proceeds to step S1107. In contrast, when the system control unit 109 determines that no moving object is detected in the captured image (NO in step S1106), the processing proceeds to step S1108.

Figure 12A:
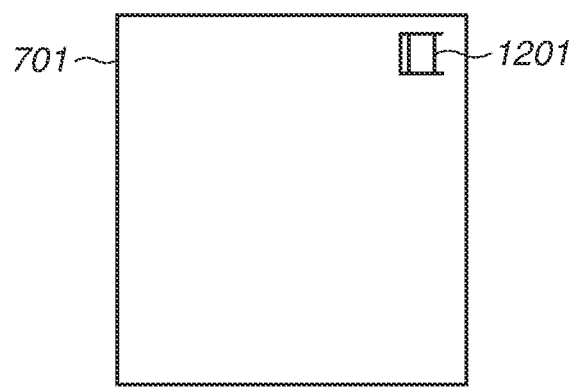
FIGS. 12A to 12C illustrate movement information for a moving object.
Figure 12B:
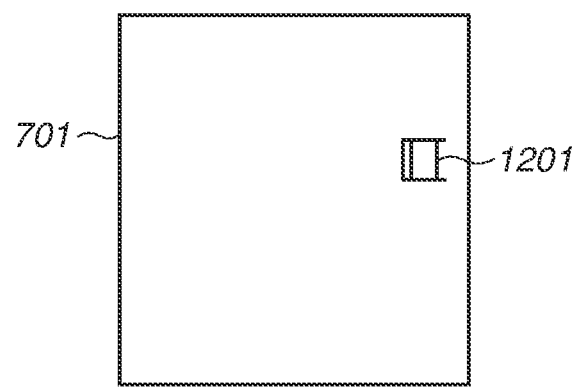
Figure 12C:
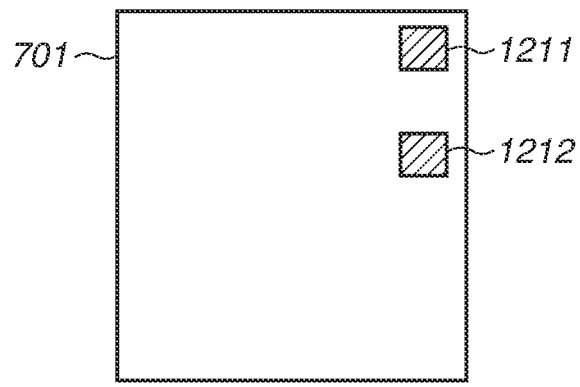

The movement information detected by the object movement detection unit 1002 will now be described with reference to FIGS. 12A to 12C. FIG. 12A illustrates a state where a chair 1201 exists at a predetermined position in the room 701. FIG. 12B illustrates a state where the chair 1201 is moved to another position. FIG. 12C illustrates an area (first existence area) 1211 where the chair 1201 has existed before the movement, and an area (second existence area) 1212 where the chair 1212 exists after the movement. When the chair 1201 is moved in this way, the object movement detection unit 1002 detects the first existence area 1211 and the second existence area 1212 illustrated in FIG. 12C as movement information for the chair 1201 (moving object) and then transmits the information to the contamination information generation unit 1003.

Referring back to FIG. 11, in step S1107, the system control unit 109 controls the contamination information generation unit 1003 to update the contamination information. In updating the contamination information, the contamination information generation unit 1003 updates the contamination information based on the movement information detected in step S1108. The update of the contamination information generated by the contamination information generation unit 1003 will be described with reference to FIGS. 13A to 13E.

Figure 13A:
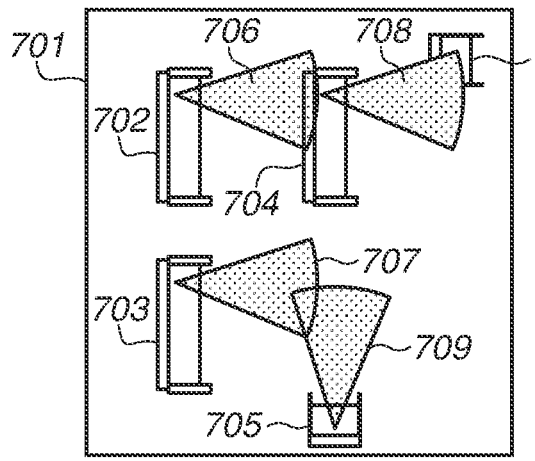
FIGS. 13A to 13E illustrate update of contamination information based on the movement information.

FIG. 13A illustrates a state where contamination information similar to that in the example illustrated in FIG. 7 is generated in a state where the chair 1201 further exists in the room 701 described above with reference to FIG. 7. FIG. 13A illustrates a state where the contaminated area 708 partly overlaps with the chair 1201.

Figure 13B:
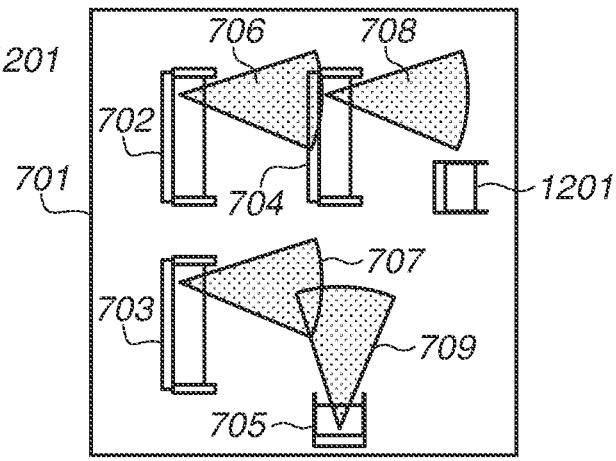

FIG. 13B illustrates a state where the chair 1201 has been moved from the state where the contamination information is generated as illustrated in FIG. 13A to another position. As illustrated in FIG. 13B, the chair 1201, having existed in a certain contaminated area before the movement, exists at a position out of the contaminated area after the movement. In this state, no contamination information is generated in the area (second existence area) where the contaminated chair 1201 exists after the movement. Thus, no correct contaminated area can be presented to the user.

Figure 13C:
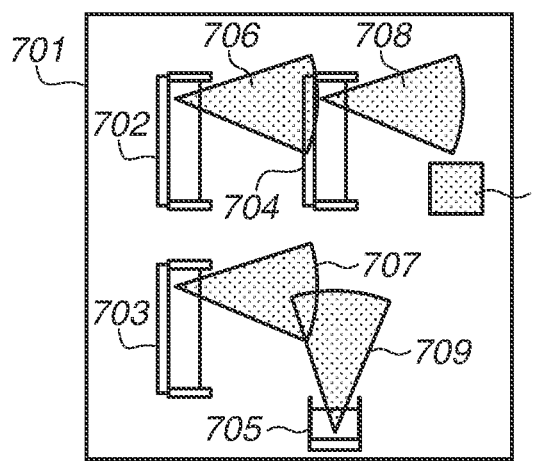

Accordingly, when at least a part of the first existence area of the detected moving object overlaps with the contaminated area, the information processing apparatus 1001 generates new contamination information in which the second existence area of the moving object is set as a contaminated area. In this example, as illustrated in FIG. 13C, the information processing apparatus 1001 generates new contamination information in which the destination existence area (second existence area) 1301 of the moving object that has existed in a certain contaminated area is set as a contaminated area. This enables presenting to the user that, even when the moving object that has existed in a certain contaminated area is moved, the movement destination is a contaminated area.

In a state illustrated in FIG. 13B, the area of the contaminated area 708 where the chair 1201 has existed before the movement still remains to be a contaminated area. However, since the chair 1201 has been moved, it is thought that the area (first existence area) where the chair 1201 has existed before the movement is no longer a contaminated area.

Figure 13D:
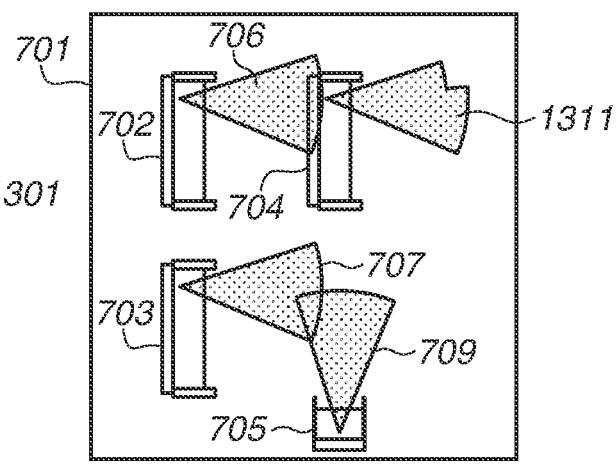

Accordingly, when the object that has existed in a certain contaminated area is moved, the information processing apparatus 1001 may update the contamination information so that the portion of the first existence area overlapping with the moving object is excluded from the contaminated areas. For example, as illustrated in FIG. 13D, the information processing apparatus 1001 updates the contamination information to change the contaminated area 708 to a contaminated area 1311 so that the existence area (first existence area) of the moving object (that has existed in a certain contaminated area) before the movement is excluded from the contaminated areas. This enables presenting to the user that, when the moving object that has existed in a certain contaminated area is moved, the existence area of the object before the movement is no longer a contaminated area. Although, in FIG. 13D, the shape of the contaminated area is changed so that the first existence area of the moving object (that has existed in a certain contaminated area) is excluded from the contaminated areas, some embodiments are not limited thereto. For example, the information processing apparatus 1001 can also update the contamination information to new contamination information by adding information indicating that the first existence area of the moving object (that has existed in a certain contaminated area) is no longer a contaminated area, to the contamination information, while maintaining the shape of the contaminated area.

When an object that has existed in a certain contaminated area is moved, the information processing apparatus 1001 may generate new contamination information in which the locus range of the movement of the object is set as a contaminated area.

Figure 13E:
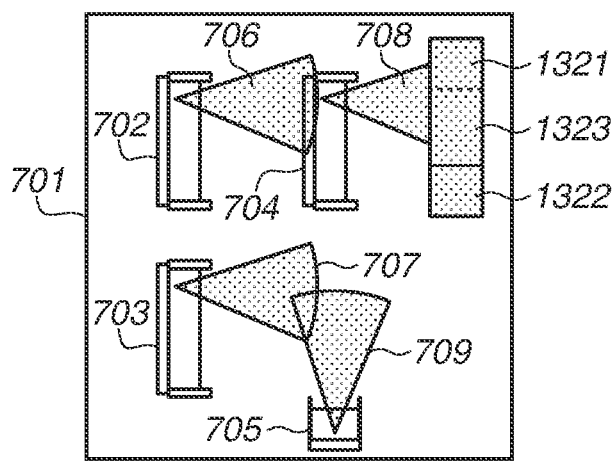

In this example case, as illustrated in FIG. 13E, the information processing apparatus 1001 generates new contamination information in which a locus range 1323 of the chair 1201 having been moved from a first existence area 1321 to a second existence area 1322 is set as a contaminated area. When an object that has existed in a certain contaminated area is moved, this processing enables presenting a moving path that may possibly be newly contaminated to the user, as a contaminated area.

Upon completion of the contamination information update based on the movement information in step S1107, as described above, the processing proceeds to step S1108.

In step S1108, the system control unit 109 confirms whether a condition for ending the storage of the contamination information is set as a predetermined storage condition and determines whether to end the storage of the contamination information.

When the system control unit 109 determines that the condition for ending the storage of the contamination information is satisfied and determines to end the storage of the contamination information (YES in step S1108), the system control unit 109 completes the contaminated area detection and generation processing. In contrast, when the system control unit 109 determines that the condition for ending the storage of the contamination information is not satisfied and determines not to end the storage of the contamination information (NO in step S1108), the processing proceeds to step S1109.

In step S1109, the system control unit 109 determines whether an information presentation instruction for requesting to present the contamination information or the combined contamination information is issued from the user via the information presentation unit 108. When the system control unit 109 determines that the information presentation instruction is issued (YES in step S1109), the system control unit 109 completes the contaminated area detection and generation processing. In contrast, when the system control unit 109 determines that no information presentation instruction is issued (NO in step S1109), the processing returns to step S1104.

According to the third exemplary embodiment, the information processing apparatus 1001 updates the contamination information according to the movement information for an object, thereby enabling the user to reliably recognize contaminated areas even after the movement of an object that has existed in a certain contaminated area.

The third exemplary embodiment has been described above centering on an example operation where, when an object existing in a certain contaminated area is moved, the stored contamination information is updated according to the movement of the object.

A fourth exemplary embodiment will be described below centering on an example operation of storing video data during the movement and image data before and after the movement when the object existing in the contaminated area is moved. The fourth exemplary embodiment is similar to the above-described third exemplary embodiment except for the contaminated area detection and generation processing performed by the information processing apparatus 1001, and descriptions thereof will be omitted. The contaminated area detection and generation processing according to the fourth exemplary embodiment will now be described.

FIG. 14 is a flowchart illustrating an example of the contaminated area detection and generation processing according to the fourth exemplary embodiment. The information processing apparatus 1001 starts the contaminated area detection and generation processing illustrated in FIG. 14, for example, when power of the apparatus is turned ON. The information processing apparatus 1001 may start the contaminated area detection and generation processing illustrated in FIG. 14 upon reception of an instruction from the user.

In step S1401, the system control unit 109 determines whether the predetermined storage condition is specified via the information presentation unit 108. The predetermined storage condition to be specified refers to, for example, the time period during which the contamination information is stored. When the system control unit 109 determines that the predetermined storage condition is specified (YES in step S1401), the processing proceeds to step S1402. In contrast, when the system control unit 109 determines that the predetermined storage condition is not specified (NO in step S1401), the processing proceeds to step S1404.

In step S1402, the system control unit 109 sets the predetermined storage condition. Upon completion of the storage condition setting, the processing proceeds to step S1403.

In step S1403, the system control unit 109 waits until the predetermined storage condition set in step S1402 is satisfied. When the predetermined storage condition is satisfied, the processing proceeds to step S1404.

In step S1404, the system control unit 109 controls the sound acquisition unit 102, the sound information generation unit 103, the sound direction detection unit 104, and the facial state detection unit 106 to perform detection processing. The detection processing in step S1404 is similar in detail to the detection processing according to the first exemplary embodiment described above with reference to FIG. 3, and descriptions thereof will be omitted. Upon completion of the detection processing, the processing proceeds to step S1405.

In step S1405, referring to the result of the detection processing performed in step S1404, the system control unit 109 controls the contamination information generation unit 1003 to perform the contamination information generation processing. The contamination information generation processing in step S1405 is similar in detail to the contamination information generation processing according to the first exemplary embodiment described above with reference to FIG. 4, and descriptions thereof will be omitted. Upon completion of the contamination information generation processing, the processing proceeds to step S1406.

In step S1406, the system control unit 109 controls the object movement detection unit 1002 to perform the moving object detection processing and determines whether a moving object is detected in the image captured by the imaging unit 105. When the system control unit 109 determines that a moving object is detected in the captured image (YES in step S1406), the processing proceeds to step S1407. In contrast, when the system control unit 109 determines that no moving object is detected in the captured image (NO in step S1406), the processing proceeds to step S1408.

In step S1407, since a moving object was detected in step S1406, the system control unit 109 stores the video data in which the object captured by the imaging unit 105 is moving and the image data before and after the movement of the object. Thus, when a moving object is detected, the system control unit 109 stores not only the updated contamination information according to the third exemplary embodiment but also the scene of the movement, as video or image data. When the contaminated area is cleaned, this processing enables presenting video or image information as supplementary information together with the contaminated area to the user. Regarding the storage of the video data and the image data, either one or both of these pieces of data may be stored according to a storage mode preselected by the user. Upon completion of the storage of the video data of the moving object and/or the image data before and after the movement thereof in step S1407, the processing proceeds to step S1408.

In step S1408, the system control unit 109 confirms whether a condition for ending the storage of the contamination information is set as a predetermined storage condition, and determines whether to end the storage of the contamination information.

When the system control unit 109 determines that the condition for ending the storage of the contamination information is satisfied and determines to end the storage of the contamination information (YES in step S1408), the system control unit 109 completes the contaminated area detection and generation processing. In contrast, when the system control unit 109 determines that the condition for ending the storage of the contamination information is not satisfied and determines not to end the storage of the contamination information (NO in step S1408), the processing proceeds to step S1409.

In step S1409, the system control unit 109 determines whether an information presentation instruction for requesting to present the contamination information or the combined contamination information is issued from the user via the information presentation unit 108. When the system control unit 109 determines that the information presentation instruction is issued (YES in step S1409), the system control unit 109 completes the contaminated area detection and generation processing. In contrast, when the system control unit 109 determines that no information presentation instruction is issued (NO in step S1409), the processing returns to step S1404.

According to the fourth exemplary embodiment, the information processing apparatus 1001 stores the video data and/or the image data according to the movement of an object, thereby enabling the user to reliably recognize contaminated areas even after the movement of an object that has existed in a certain contaminated area.

Figure 15:
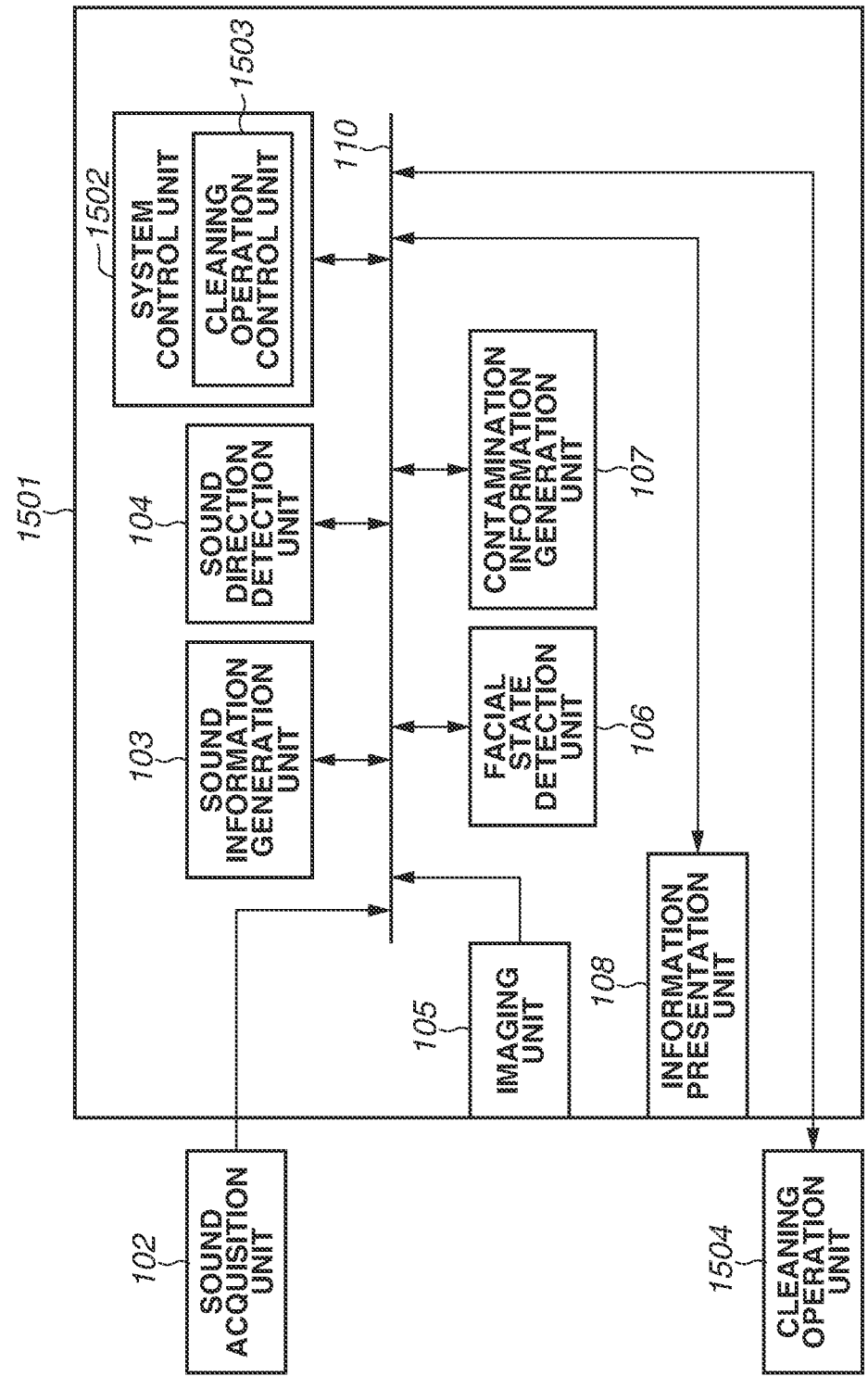
FIG. 15 illustrates an example configuration of a cleaning apparatus according to a fifth exemplary embodiment.

FIG. 15 is a block diagram illustrating an example configuration of a cleaning apparatus 1501 according to a fifth exemplary embodiment. Referring to FIG. 15, components having identical functions to those illustrated in FIG. 1 are assigned the same reference numerals and duplicated descriptions thereof will be omitted. The cleaning apparatus 1501 includes a sound acquisition unit 102, a sound information generation unit 103, a sound direction detection unit 104, an imaging unit 105, a facial state detection unit 106, a contamination information generation unit 107, an information presentation unit 108, a communication bus 110, a system control unit 1502, and a cleaning operation unit 1504. The term "cleaning" comprehensively means overall actions intending to suppress bacteria or viruses (e.g., bacteria elimination, antisepsis, sterilization, antibacterial actions, virus removal, virus killing, and disinfection).

The system control unit 1502 having a similar function to the system control unit 109 according to the first exemplary embodiment controls the entire cleaning apparatus 1501 via the communication bus 110.

The system control unit 1502 implements each piece of processing (described below) by executing a program recorded in a storage unit such as a nonvolatile memory (not illustrated). The system control unit 1502 includes a cleaning operation control unit 1503.

The cleaning operation control unit 1503 controls operation of the cleaning operation unit 1504 via the communication bus 110 by executing a program recorded in a storage unit such as a nonvolatile memory (not illustrated).

The cleaning operation unit 1504 is a cleaning machine controlled by the cleaning operation control unit 1503. The cleaning operation unit 1504 is, for example, a nebulizer for spraying the cleaning agent such as alcohol in a mist form, or an irradiator for radiating light having a cleaning effect, such as an ultraviolet ray. The cleaning operation unit 1504 may also be a self-propelled robot cleaner. According to the fifth exemplary embodiment, the cleaning operation unit 1504 is, for example, a cleaning agent nebulizer installed on the ceiling of the room 701, capable of controlling the spray angle and the spray time duration. The spray angle of the cleaning agent and the spray range thereof in the room 701 are associated with each other as data in a storage area (not illustrated). The spray time during which the contaminated area can be sufficiently cleaned is to be acquired in a prior experiment and is stored in a storage area (not illustrated) as data.

Operation of the cleaning apparatus 1501 will now be described.

The cleaning apparatus 1501 performs the contaminated area detection and contamination information generation processing. The contaminated area detection and generation processing performed by the cleaning apparatus 1501 is similar to the contaminated area detection and generation processing according to the first exemplary embodiment described above with reference to FIGS. 2 to 4, and thus descriptions thereof will be omitted.

Figure 16:
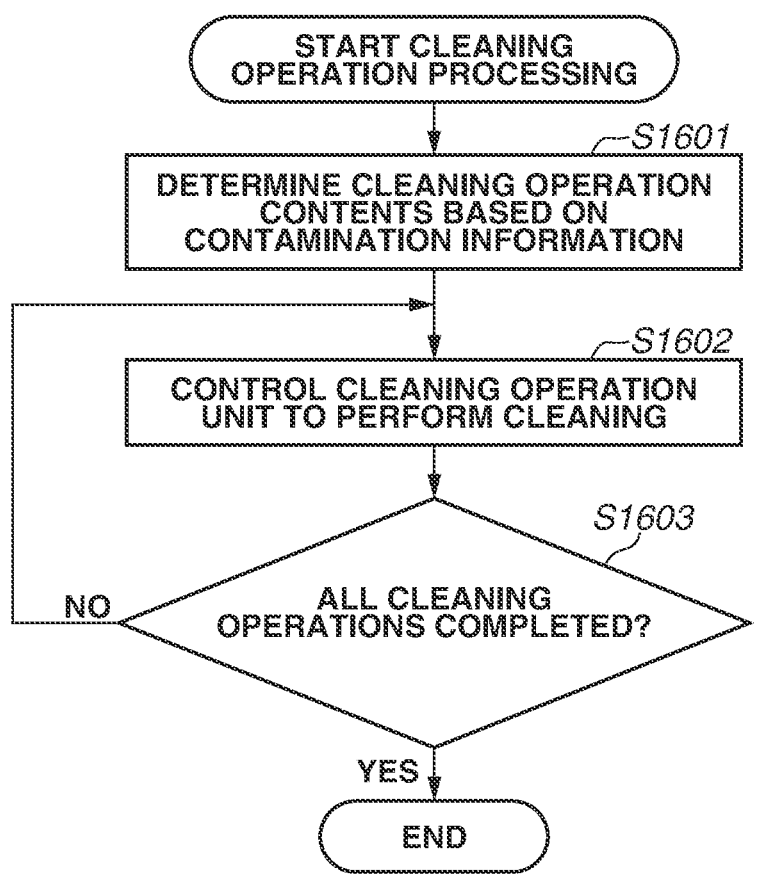
FIG. 16 is a flowchart illustrating an example of cleaning operation processing according to the fifth exemplary embodiment.

The cleaning operation performed by the cleaning apparatus 1501 based on the contamination information generated in the contaminated area detection and generation processing will be described with reference to FIGS. 16 and 17. FIG. 16 is a flowchart illustrating an example of the cleaning operation processing. For example, when a predetermined time duration has elapsed since the cleaning apparatus 1501 completes the contaminated area detection and generation processing, the cleaning apparatus 1501 automatically starts the cleaning operation processing illustrated in FIG. 16. The cleaning apparatus 1501 may also start the cleaning operation processing illustrated in FIG. 16 upon reception of an instruction from the user.

When the cleaning apparatus 1501 starts the cleaning operation processing, then in step S1601, the cleaning operation control unit 1503 determines the operation contents of the cleaning operation unit 1504 based on the contamination information generated by the contamination information generation unit 107. Examples of operation contents include, for example, the spray angle and the spray time of the cleaning agent used in the cleaning operation unit 1504. In this case, the cleaning operation control unit 1503 determines the spray angle such that the spray range of the cleaning agent sufficiently covers the shape of the contaminated area included in the contamination information. The cleaning operation control unit 1503 also determines the spray time of the cleaning agent so that the contaminated area is sufficiently cleaned. Upon completion of the determination of the operation contents of the cleaning operation unit 1504, the processing proceeds to step S1602.

In step S1602, the cleaning operation control unit 1503 controls the cleaning operation unit 1504 to perform cleaning based on the operation contents determined in step S1601. The cleaning operation control unit 1503 instructs the cleaning operation unit 1504 to adjust the spray angle of the cleaning operation unit 1504 and to spray the cleaning agent for a predetermined time duration based on the determined operation contents. Upon completion of the control of the cleaning operation unit 1504 according to the operation contents, the processing proceeds to step S1603.

In step S1603, the cleaning operation control unit 1503 determines whether the cleaning operation unit 1504 has completed all of the operation contents determined in step S1601. When the cleaning operation control unit 1503 determines that any of the operation contents is incomplete (NO in step S1603), the processing returns to step S1602. Then, the cleaning operation control unit 1503 continues the control of the operation of the cleaning operation unit 1504. In contrast, when the cleaning operation control unit 1503 determines that all of the operation contents determined in step S1601 are completed (YES in step S1603), the cleaning operation control unit 1503 completes the cleaning operation processing.

Figure 17:
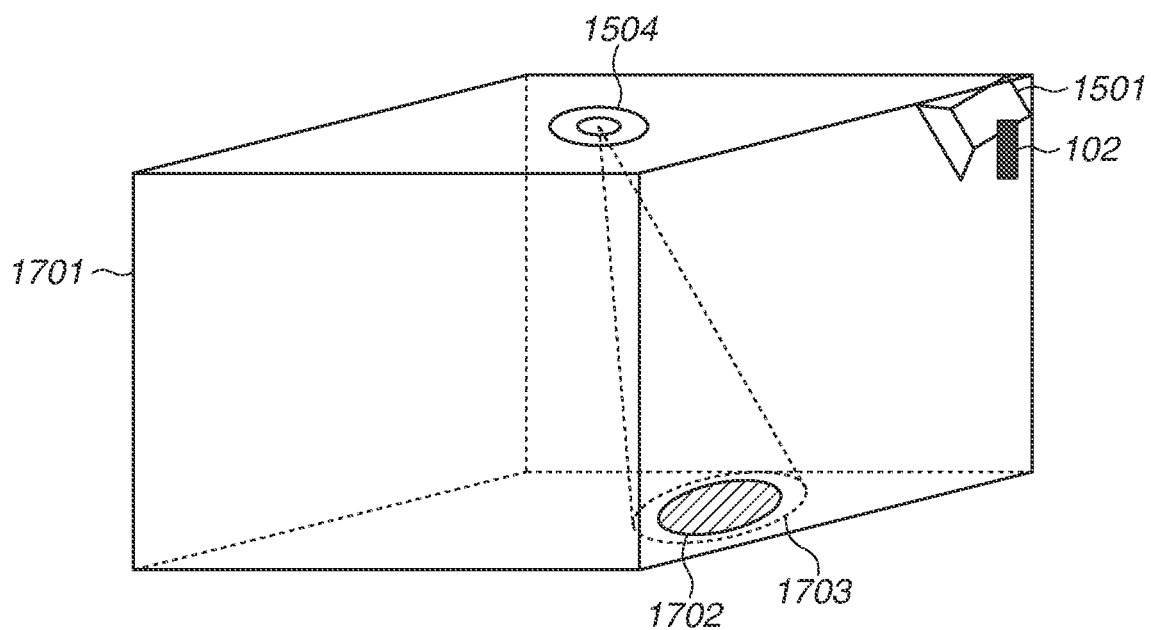
FIG. 17 illustrates the cleaning operation according to the fifth exemplary embodiment.

FIG. 17 illustrates a cleaning operation performed by the cleaning apparatus 1501 illustrated in FIG. 16 with reference to an example where the cleaning apparatus 1501 is installed in a room 1701. The sound acquisition unit 102 and the cleaning operation unit 1504 included in the cleaning apparatus 1501 are visible from the outside, and are connected with other components of the cleaning apparatus 1501 via a communication unit (not illustrated). A contaminated area 1702 indicates the shape of the contaminated area included in the contamination information generated in the contaminated area detection and generation processing and then stored. A spray range 1703 indicates the shape of the spray range of the cleaning agent obtained by the operation of the cleaning operation unit 1504 described in steps S1601 and S1602 in FIG. 16.

In step S1601 in FIG. 16, the cleaning operation control unit 1503 determines the spray angle of the cleaning operation unit 1504 so that the spray range 1703 of the cleaning agent sufficiently covers the entire contaminated area 1702. In step S1602 in FIG. 16, the cleaning operation control unit 1503 controls the spray angle of the cleaning operation unit 1504 to spray the cleaning agent based on the spray angle determined in step S1601. This enables the cleaning apparatus 1501 to spray the cleaning agent to the entire contaminated area 1702. This also enables restricting the spraying of the cleaning agent for non-contaminated areas outside the contaminated area 1702. By performing such processing, the cleaning apparatus 1501 can automatically clean the areas contaminated by droplets while restricting the amount of the cleaning agent.

Prior to the cleaning operation processing according to the present exemplary embodiment, the cleaning apparatus 1501 may or may not perform the contamination information presentation processing described above with reference to FIG. 6 similar to that in the first exemplary embodiment. When the contamination information presentation processing has been performed, the cleaning apparatus 1501 starts the cleaning operation processing illustrated in FIG. 16 in a state where the contaminated area 1702 illustrated in FIG. 17 is presented. The cleaning apparatus 1501 completes the contamination information presentation processing after completion of the cleaning operation processing illustrated in FIG. 16. Such processing makes it easier for the user to determine whether the contaminated area has been cleaned by the cleaning apparatus 1501.

According to the fifth exemplary embodiment, the cleaning apparatus 1501 detects a contaminated area and then automatically cleans only the area, making it possible to recognize the contaminated area to which droplets scattered from a person adhere and efficiently performing the cleaning.

Figure 18:
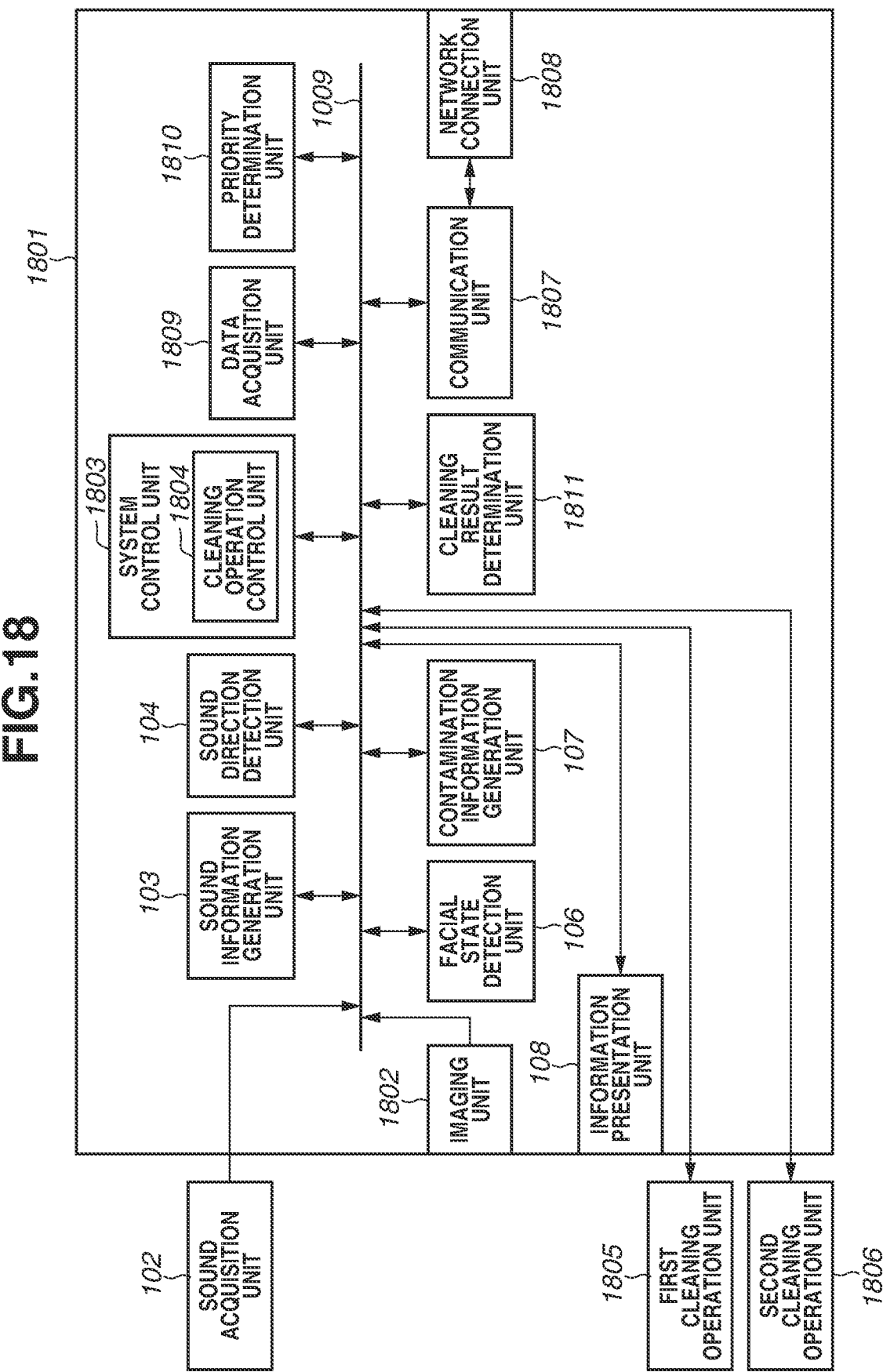
FIG. 18 illustrates an example configuration of a cleaning apparatus according to a sixth exemplary embodiment.

The cleaning apparatus according to a sixth exemplary embodiment controls a plurality of cleaning operation units to perform the cleaning on a plurality of contaminated areas. FIG. 18 is a block diagram illustrating an example configuration of a cleaning apparatus 1801 according to the sixth exemplary embodiment. Referring to FIG. 18, components having identical functions to those illustrated in FIG. 1 are assigned the same reference numerals and duplicated descriptions thereof will be omitted. The cleaning apparatus 1801 includes a sound acquisition unit 102, a sound information generation unit 103, a sound direction detection unit 104, a facial state detection unit 106, a contamination information generation unit 107, an information presentation unit 108, a communication bus 110, an imaging unit 1802, and a system control unit 1803. The cleaning apparatus 1801 also includes a first cleaning operation unit 1805, a second cleaning operation unit 1806, a communication unit 1807, a network connection unit 1808, a data acquisition unit 1809, a priority determination unit 1810, and a cleaning result determination unit 1811.

The imaging unit 1802 having a similar function to the imaging unit 105 according to the first exemplary embodiment captures a subject to generate an image of the subject. The imaging unit 1802 can acquire body temperature information for the subject.

The system control unit 1803 having a similar function to the system control unit 109 according to the first exemplary embodiment controls the entire cleaning apparatus 1801 via the communication bus 110.

The system control unit 1803 implements each piece of processing (described below) by executing a program recorded in a storage unit such as a nonvolatile memory (not illustrated). The system control unit 1803 also includes a cleaning operation control unit 1804.

The cleaning operation control unit 1804 controls the operations of the first cleaning operation unit 1805 and the second cleaning operation unit 1806 via the communication bus 110 by executing a program recorded in a storage unit such as a nonvolatile memory (not illustrated).

The first cleaning operation unit 1805 and the second cleaning operation unit 1806 are cleaning machines controlled by the cleaning operation control unit 1804. For example, each of the first cleaning operation unit 1805 and the second cleaning operation unit 1806 is, for example, a nebulizer for spraying a cleaning agent, such as alcohol, in a mist form, or an irradiator for radiating light having a cleaning effect, such as an ultraviolet ray. Each of the first cleaning operation unit 1805 and the second cleaning operation unit 1806 may also be a self-propelled robot cleaner. According to the sixth exemplary embodiment, for example, the first cleaning operation unit 1805 is a cleaning agent nebulizer installed on the ceiling of the room 1701, capable of controlling the spray angle and the spray time duration. The second cleaning operation unit 1806 is a self-propelled robot capable of irradiating the floor surface with an ultraviolet ray.

The communication unit 1807 is a communication module capable of connecting with a network via the network connection unit 1808.

The network connection unit 1808 is an interface for connecting the communication unit 1807 to the network.

The data acquisition unit 1809 connects with a network via the communication unit 1807 and the network connection unit 1808 to acquire data for a subject who entered the room 1701. The data acquisition unit 1809 stores the acquired data for the subject and the contamination information generated by the contamination information generation unit 107 in an associated way. Examples of the data for the subject include, for example, medical conditions of the subject (or medical history, symptoms, or doctor's diagnosis result). The data acquisition unit 1809 also detects a subject from the image captured by the imaging unit 1802 and stores the body temperature information for the subject and the contamination information in an associated way.

The priority determination unit 1810 determines the cleaning priority for each contaminated area based on the data stored in the data acquisition unit 1809. The cleaning result determination unit 1811 determines a cleaning result indicating whether cleaning operation is sufficient based on the priority determined by the priority determination unit 1810 and the operation contents for cleaning by the first cleaning operation unit 1805 and the second cleaning operation unit 1806.

Figure 19:
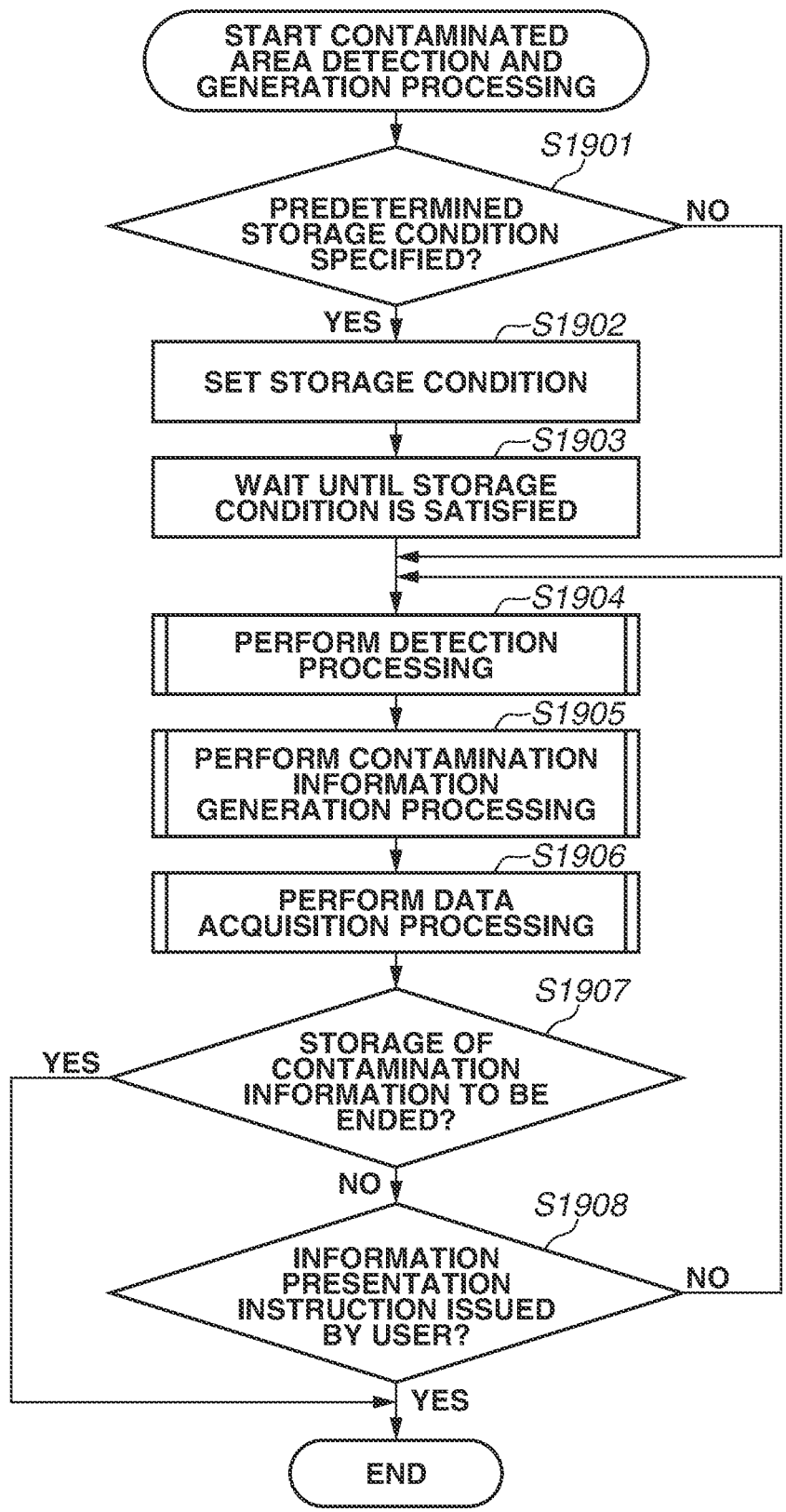
FIG. 19 is a flowchart illustrating an example of contaminated area detection and generation processing according to the sixth exemplary embodiment.

The contaminated area detection and generation processing performed by the cleaning apparatus 1801 will now be described with reference to FIG. 19. FIG. 19 is a flowchart illustrating an example of the contaminated area detection and generation processing according to the sixth exemplary embodiment. The cleaning apparatus 1801 starts the contaminated area detection and generation processing illustrated in FIG. 19, for example, when power of the apparatus is turned ON. The cleaning apparatus 1801 may start the contaminated area detection and generation processing illustrated in FIG. 19 upon reception of an instruction from the user.

In step S1901, the system control unit 1803 determines whether a predetermined storage condition is specified via the information presentation unit 108. The predetermined storage condition to be specified refers to, for example, the time period during which the contamination information is stored. When the system control unit 1803 determines that the predetermined storage condition is specified (YES in step S1901), the processing proceeds to step S1902. In contrast, when the system control unit 1803 determines that the predetermined storage condition is not specified (NO in step S1901), the processing proceeds to step S1904.

In step S1902, the system control unit 1803 sets the predetermined storage condition. Upon completion of the storage condition setting, the processing proceeds to step S1903.

In step S1903, the system control unit 1803 waits until the predetermined storage condition set in step S1902 is satisfied. When the predetermined storage condition is satisfied, the processing proceeds to step S1904.

In step S1904, the system control unit 1803 performs detection processing by controlling the sound acquisition unit 102, the sound information generation unit 103, the sound direction detection unit 104, and the facial state detection unit 106. The detection processing in step S1904 is similar in detail to the detection processing according to the first exemplary embodiment described above with reference to FIG. 3, and descriptions thereof will be omitted. Upon completion of the detection processing, the processing proceeds to step S1905.

In step S1905, referring to the result of the detection processing performed in step S1104, the system control unit 1803 controls the contamination information generation unit 107 to perform the contamination information generation processing. The contamination information generation processing in step S1905 is similar in detail to the contamination information generation processing according to the first exemplary embodiment described above with reference to FIG. 4, and descriptions thereof will be omitted. Upon completion of the contamination information generation processing, the processing proceeds to step S1906.

In step S1906, the system control unit 1803 controls the data acquisition unit 1809 to perform data acquisition processing. The data acquisition processing in step S1906 will be described in detail below with reference to FIG. 20. Upon completion of the data acquisition processing, the processing proceeds to step S1907.

In step S1907, the system control unit 1803 confirms whether a condition for ending the storage of the contamination information is set as a predetermined storage condition and determines whether to end the storage of the contamination information. When the system control unit 1803 determines that the condition for ending the storage of the contamination information is satisfied and determines to end the storage of the contamination information (YES in step S1907), the system control unit 1803 completes the contaminated area detection and generation processing. In contrast, when the system control unit 1803 determines that the condition for ending the storage of the contamination information is not satisfied and determines not to end the storage of the contamination information (NO in step S1907), the processing proceeds to step S1908.

In step S1908, the system control unit 1803 determines whether an information presentation instruction for requesting to present the contamination information or the combined contamination information is issued from the user via the information presentation unit 108. When the system control unit 1803 determines that the information presentation instruction is issued (YES in step S1908), the system control unit 1803 completes the contaminated area detection and generation processing. In contrast, when the system control unit 1803 determines that no information presentation instruction is issued (NO in step S1908), the processing returns to step S1904.

Figure 20:
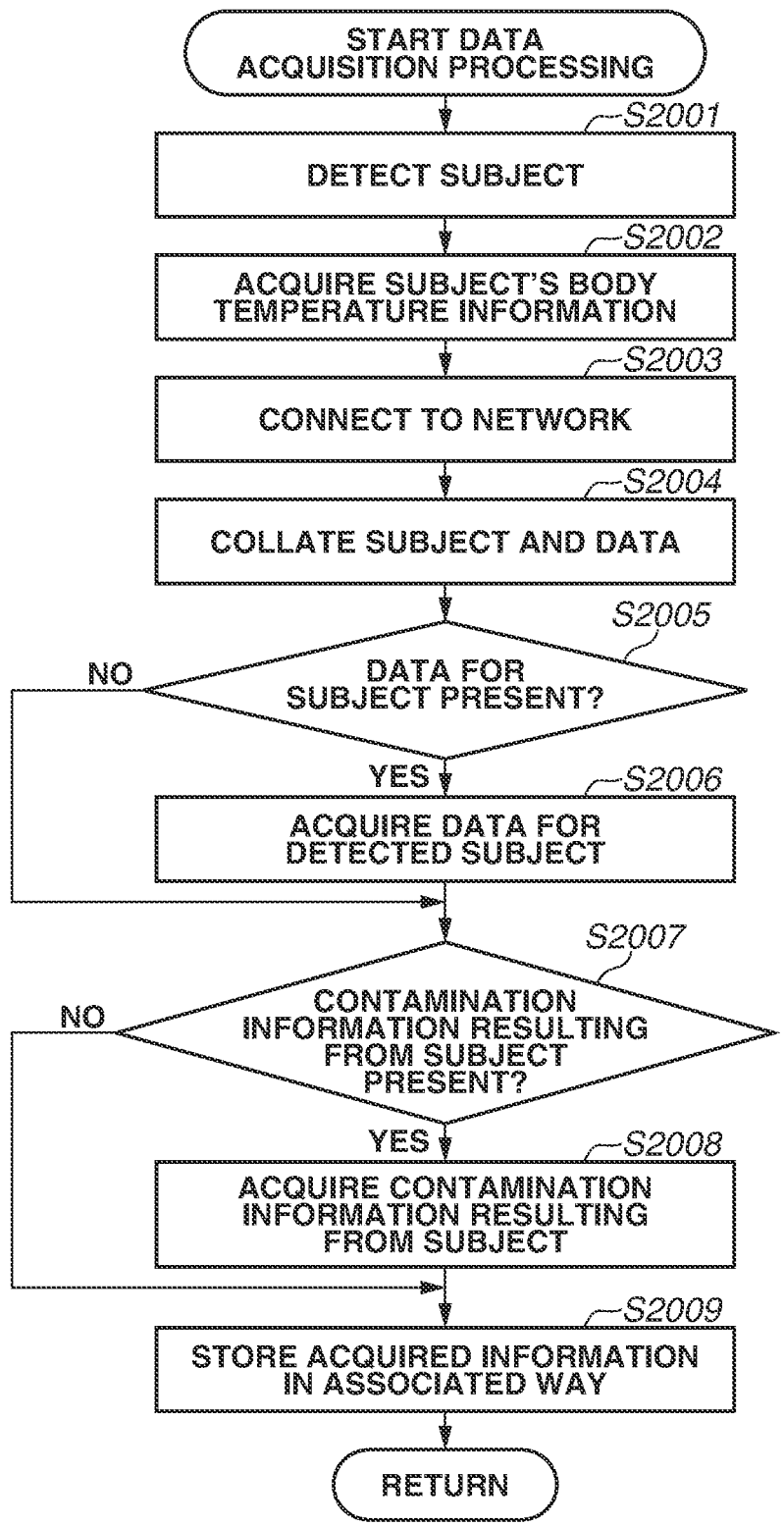
FIG. 20 is a flowchart illustrating an example of data acquisition processing according to the sixth exemplary embodiment.

The data acquisition processing in step S1906 in FIG. 19 will now be described with reference to FIG. 20. FIG. 20 is a flowchart illustrating an example of the data acquisition processing. The data acquisition unit 1809 performs the processing of the flowchart illustrated in FIG. 20 under the control of the system control unit 1803.

When the data acquisition processing is started, then in step S2001, the data acquisition unit 1809 detects a subject. This subject is identical to the subject having been subjected to the detection processing in steps S1904 and S1905. Upon completion of the detection of a subject, the processing proceeds to step S2002.

In step S2002, the data acquisition unit 1809 acquires the body temperature information for the subject from the imaging unit 1802. Upon completion of the acquisition of the body temperature information for the subject, the processing proceeds to step S2003.

In step S2003, the data acquisition unit 1809 connects with the network via the communication unit 1807 and the network connection unit 1808. Upon completion of network connection, the processing proceeds to step S2004.

In step S2004, the data acquisition unit 1809 collates the subject detected in step S2001 with data of the disease for the subject, on the connected network. For example, the data acquisition unit 1809 accesses an electronic chart database and collates the detected subject with the medical conditions or diagnosis result of the subject. Upon completion of the collation between the subject and the data, the processing proceeds to step S2005.

In step S2005, the data acquisition unit 1809 determines whether the data for the detected subject is present as a result of the collation performed in step S2004. When the data acquisition unit 1809 determines that the data for the detected subject is present (YES in step S2005), the processing proceeds to step S2006. In contrast, when the data acquisition unit 1809 determines that the data for the detected subject is absent (NO in step S2005), the processing proceeds to step S2007.

In step S2006, the data acquisition unit 1809 acquires the data for the detected subject. Upon completion of the acquisition of the data for the detected subject, the processing proceeds to step S2007.

In step S2007, the data acquisition unit 1809 determines whether the contamination information resulting from the detected subject is present in the contamination information stored in the contamination information generation unit 107.

When the data acquisition unit 1809 determines that the contamination information resulting from the detected subject is present (YES in step S2007), the processing proceeds to step S2008. In contrast, when the data acquisition unit 1809 determines that the contamination information resulting from the detected subject is absent (NO in step S2007), the processing proceeds to step S2009.

In step S2008, the data acquisition unit 1809 acquires the contamination information resulting from the detected subject. Upon completion of the acquisition of the contamination information resulting from the detected subject, the processing proceeds to step S2009.

In step S2009, the data acquisition unit 1809 stores each piece of the acquired information in an associated way. In this case, the correspondence between pieces of the stored information can be represented in an associated way as in the table illustrated in FIG. 21A. FIG. 21A illustrates data of the temperature information, medical conditions, and contamination information for four different subjects (A to D) stored in an associated way. Contaminated areas A, B, and C will be described below.

The cleaning operation performed by the cleaning apparatus 1801 will now be described with reference to FIGS. 22 and 23. FIG. 22 illustrates the cleaning operation performed by the cleaning apparatus 1801. FIG. 22 illustrates a state where three different contaminated areas (contaminated areas A, B, and C) resulting from a person (not illustrated) are present in a room 2201 where the cleaning apparatus 1801 is installed. Referring to FIG. 22, configurations identical to those of the cleaning apparatus 1801 illustrated in FIG. 18 are assigned the same reference numerals, and descriptions thereof will be omitted.

A contaminated area 2202 indicates the shape of the contaminated area included in the contamination information resulting from the subject A. The contaminated area 2202 is the contaminated area A in the table illustrated in FIG. 21A. A spray range 2203 indicates the shape of the spray range of the cleaning agent performed on the contaminated area 2202 by the first cleaning operation unit 1805.

A contaminated area 2204 indicates the shape of the contaminated area included in the contamination information resulting from the subject C. The contaminated area 2204 is the contaminated area C in the table illustrated in FIG. 21A. A spray range 2205 indicates the shape of the spray range of the cleaning agent performed on the contaminated area 2204 by the first cleaning operation unit 1805.

A contaminated area 2206 indicates the shape of the contaminated area included in the contamination information resulting from the subject B. The contaminated area 2206 is the contaminated area B in the table illustrated in FIG. 21A. The contaminated area 2206 is placed at a position below a stillage 2207 where the first cleaning operation unit 1805 cannot spray the cleaning agent.

This completes the descriptions of the status of the room 2201 including the cleaning apparatus 1801 according to the present exemplary embodiment.

Figure 23:
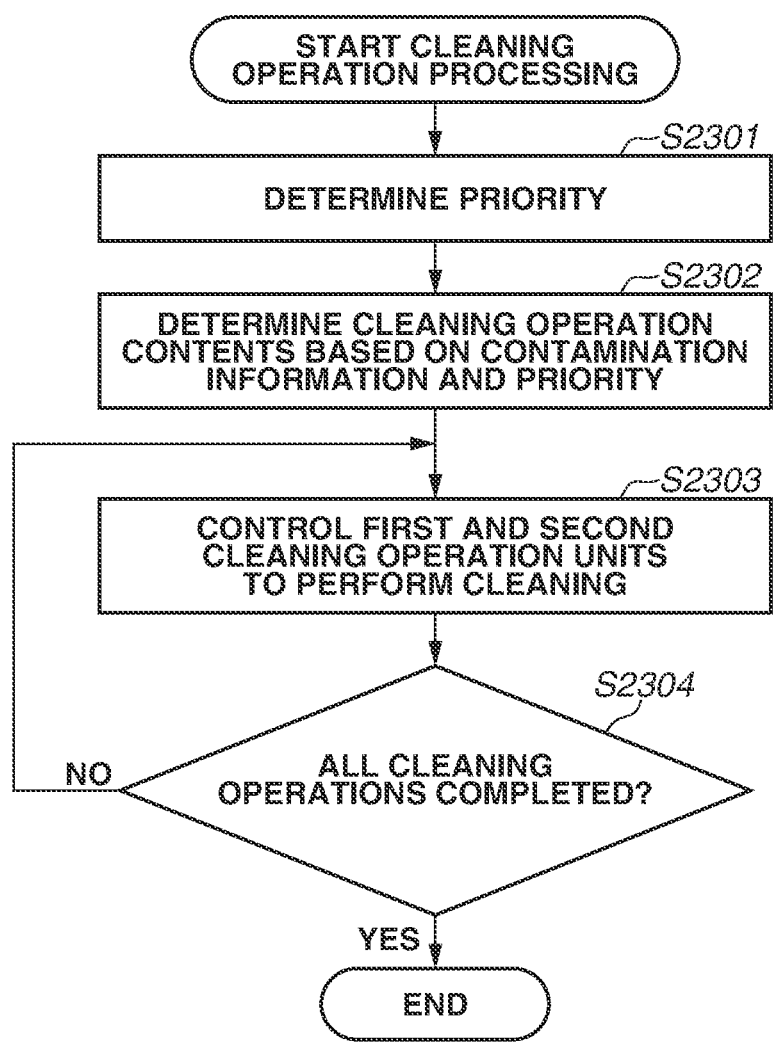
FIG. 23 is a flowchart illustrating an example of cleaning operation processing according to the fifth exemplary embodiment.

FIG. 23 is a flowchart illustrating an example of the cleaning operation processing performed by the cleaning apparatus 1801. For example, after the cleaning apparatus 1801 completes the contaminated area detection and generation processing illustrated in FIG. 19, the cleaning apparatus 1801 automatically starts the cleaning operation processing illustrated in FIG. 23 when a predetermined time duration has elapsed. The cleaning apparatus 1801 may also start the cleaning operation processing illustrated in FIG. 23 upon reception of an instruction from the user.

When the cleaning operation processing is started, then in step S2301, the priority determination unit 1810 refers to the data stored in the data acquisition unit 1809 and sets the priority for cleaning each contaminated area based on the body temperature information and the medical conditions of the subject. For example, the priorities when the data illustrated in FIG. 21A is referred to are as illustrated in FIG. 21B. These priorities are determined by a program developed based on specialized experiences. For example, if a predetermined body temperature is exceeded, a higher priority is set to the contaminated area resulting from a subject with a higher body temperature. In addition, a higher priority is set to the contaminated area resulting from a subject in medical conditions with a higher risk of infection. Upon completion of the cleaning priority setting, the processing proceeds to step S2302.

In step S2302, the cleaning operation control unit 1804 determines the operation contents of the first cleaning operation unit 1805 and the second cleaning operation unit 1806 based on the contamination information and the priority set in step S2301.

Firstly, the cleaning operation control unit 1804 determines the operation contents of the first cleaning operation unit 1805. In the case of the example illustrated in FIG. 22, the first cleaning operation unit 1805 can clean the contaminated areas 2202 and 2204. A higher priority is set to the contaminated area 2204 (contaminated area C) than to the contaminated area 2202 (contaminated area A). Thus, the operation contents of the first cleaning operation unit 1805 include an operation for spraying the cleaning agent to the contaminated area 2204 for a first predetermined time duration. Upon completion of the spraying of the cleaning agent to the contaminated area 2204, the first cleaning operation unit 1805 performs an operation for spraying the cleaning agent to the contaminated area 2202 for a second predetermined time duration which is shorter than the first predetermined time duration.

Then, the cleaning operation control unit 1804 determines the operation contents of the second cleaning operation unit 1806. Referring to the example illustrated in FIG. 22, the second cleaning operation unit 1806 can clean the contaminated areas 2204 and 2206. A higher priority is set to the contaminated area 2204 (contaminated area C) than to the contaminated area 2206 (contaminated area B). However, since the first cleaning operation unit 1805 firstly sprays the cleaning agent to the contaminated area 2204, the operation contents of the second cleaning operation unit 1806 includes an operation of irradiating the contaminated area 2206 with an ultraviolet ray for a third predetermined time duration.

When the first cleaning operation unit 1805 completes the spraying of the cleaning agent to the contaminated area 2204 after completion of the ultraviolet radiation to the contaminated area 2206, the operation contents of the first cleaning operation unit 1805 include an operation for irradiating the contaminated area 2204 with an ultraviolet ray for a fourth predetermined time duration which is longer than the third predetermined time duration.

Upon completion of the determination of the operation contents of the first cleaning operation unit 1805 and the second cleaning operation unit 1806 in this way, the processing proceeds to step S2303.

In step S2303, the cleaning operation control unit 1804 controls the first cleaning operation unit 1805 and second cleaning operation unit 1806 to perform cleaning based on the operation contents determined in step S2302. Upon completion of the control of the first cleaning operation unit 1805 and the second cleaning operation unit 1806 based on the operation contents, the processing proceeds to step S2304.

In step S2304, the cleaning operation control unit 1804 determines whether the first cleaning operation unit 1805 and the second cleaning operation unit 1806 have completed all of the operation contents determined in step S2302. When the cleaning operation control unit 1804 determines that not all of the operation contents are completed, i.e., any of the operation contents is incomplete (NO in step S2304), the processing returns to step S2303. In step S2303, the cleaning operation control unit 1804 continues the cleaning operation. In contrast, when the cleaning operation control unit 1804 determines that all of the operation contents determined in step S2302 are completed (YES in step S2304), the cleaning operation control unit 1804 completes the cleaning operation processing.

By performing the above-described processing, the cleaning apparatus 1801 can efficiently and automatically clean the areas contaminated by droplets.

Figure 24:
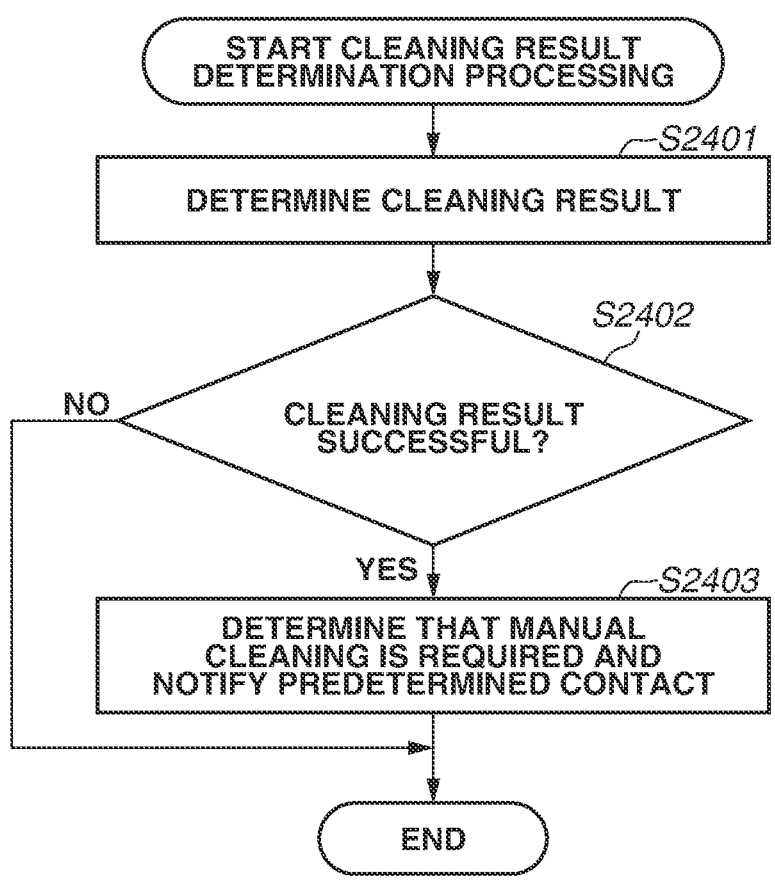
FIG. 24 is a flowchart illustrating an example of cleaning result determination processing according to the sixth exemplary embodiment.

Cleaning result determination processing performed by the cleaning result determination unit 1811 will now be described with reference to FIG. 24. FIG. 24 is a flowchart illustrating an example of the cleaning result determination processing.

When the cleaning result determination processing is started, then in step S2401, the cleaning result determination unit 1811 determines the cleaning result. The cleaning result determination unit 1811 determines the cleaning result based on the priority data illustrated in FIG. 21B and the cleaning operation contents of the first cleaning operation unit 1805 and the second cleaning operation unit 1806.

For example, as illustrated in FIG. 21C, both the spraying of the cleaning agent and the ultraviolet irradiation are completed for the contaminated area C having the "High" priority. Thus, the cleaning result determination is successful. However, for example, when the priority of the contaminated area B is also "High", as illustrated in FIG. 21D, only the ultraviolet irradiation is completed for the contaminated area B. Thus, the cleaning result determination is failed (manual cleaning required).

Upon completion of the cleaning result determination, the processing proceeds to step S2402.

In step S2402, the cleaning result determination unit 1811 determines whether the cleaning result determination is successful. When the cleaning result determination unit 1811 determines that the cleaning result determination is not successful (NO in step S2402), the processing proceeds to step S2403. In step S2403, the cleaning result determination unit 1811 determines that the manual cleaning is required, notifies a predetermined contact, and then completes the cleaning result determination processing. When the cleaning result determination unit 1811 determines that the cleaning result determination is successful (YES in step S2402), the cleaning result determination unit 1811 completes the cleaning result determination processing.

This processing brings efficient cleaning even in a case of an insufficient cleaning result through mechanical cleaning. Assume an example case where the cleaning result determination unit 1811 notifies a predetermined contact, and a designated sanitation worker is dispatched to perform the cleaning. In this case, the information processing apparatus 101 performs the contamination information presentation processing according to the first exemplary embodiment, enabling the sanitation worker to recognize the contaminated areas and efficiently perform the cleaning.

The first cleaning operation unit 1805 may be a cleaning agent nebulizer capable of selecting a type of cleaning agent from a plurality of types of cleaning agents and then spraying the cleaning agent. In this case, the first cleaning operation unit 1805 may select the type of the cleaning agent to be sprayed, based on the data as illustrated in FIG. 21B. This processing allows further improvement of the cleaning effect for each contaminated area. When a plurality of cleaning operation units can perform the cleaning as is the case with the contaminated area 2204 illustrated in FIG. 22, there may be one or more cleaning operation units that do not clean any contaminated area depending on the priority. This processing enables completing cleaning in a short time.

According to the sixth exemplary embodiment, the cleaning apparatus 1801 sets the priority for each of the detected contaminated areas and selects a most suitable cleaning method, thus enabling efficient cleaning.

Figure 25:
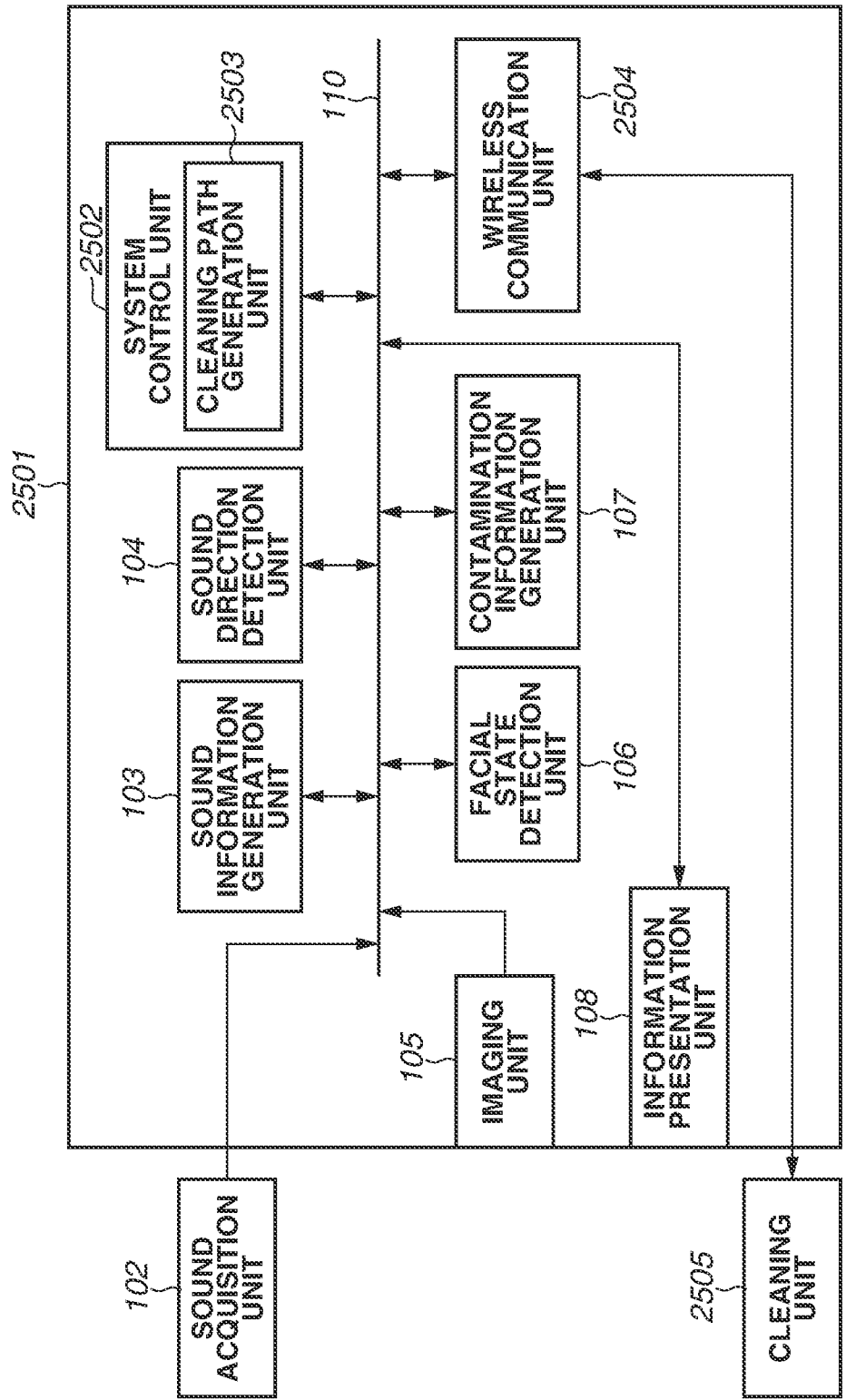
FIG. 25 is a block diagram illustrating an example configuration of an information processing apparatus according to a seventh exemplary embodiment.

FIG. 25 is a block diagram illustrating an example configuration of an information processing apparatus 2501 according to a seventh exemplary embodiment. Referring to FIG. 25, components having identical functions to those illustrated in FIG. 1 are assigned the same reference numerals and duplicated descriptions thereof will be omitted. The information processing apparatus 2501 includes a sound acquisition unit 102, a sound information generation unit 103, a sound direction detection unit 104, an imaging unit 105, a facial state detection unit 106, a contamination information generation unit 107, an information presentation unit 108, and a communication bus 110. The information processing apparatus 2501 also includes a system control unit 2502, a wireless communication unit 2504, and a cleaning unit 2505.

The system control unit 2502 has a similar function to the system control unit 109 according to the first exemplary embodiment and controls the entire information processing apparatus 2501 via the communication bus 110. The system control unit 2502 also includes a cleaning path generation unit 2503.

The cleaning path generation unit 2503 generates a cleaning path of the cleaning unit 2505 via the communication bus 110 by executing a program recorded in a storage unit such as a nonvolatile memory (not illustrated). The cleaning path generation unit 2503 generates a cleaning path to enable the cleaning unit 2505 to clean the detected contaminated areas in a shortest time or a shortest path. The cleaning path generation unit 2503 generates a cleaning path so that the contaminated areas are cleaned in a preferential way. When cleaning a detected contaminated area, cleaning on a one-way basis is recommended. This is because, in a case where an area is wiped and not contaminated or a cleaned area is cleaned, contaminated areas may possibly be expanded. One-way cleaning will be specifically described below with reference to the accompanying drawings.

The wireless communication unit 2504 includes an antenna for wireless communication and a communication control unit. The wireless communication unit 2504 wirelessly communicates with the cleaning unit 2505 by using, for example, a Wireless Local Area Network (Wireless LAN). The information processing apparatus 2501 is capable of wirelessly communicating with electronic devices conforming to a wireless LAN. The system control unit 2502 transmits cleaning path information generated by the cleaning path generation unit 2503 to the cleaning unit 2505 via the wireless communication unit 2504. The cleaning unit 2505 can also transmit information indicating the cleaning status to the system control unit 2502 through communication using the wireless LAN.

The cleaning unit 2505 performs cleaning based on the cleaning path generated by the cleaning path generation unit 2503. The cleaning unit 2505 is, for example, a self-propelled robot cleaner. Cleaning according to the seventh exemplary embodiment refers to wiping, for example, the floor. The cleaning unit 2505 performs the cleaning by using a cleaning sheet having sanitization and/or sterilization effects for wiping. The cleaning sheet may be suitably changeable. If the cleaning sheet is unchangeable, the cleaning unit 2505 may be provided with a mechanism for sanitizing and/or sterilizing the cleaning sheet itself. The cleaning unit 2505 can perform cleaning by using not only a cleaning sheet having sanitization and/or sterilization effects but also a cleaning sheet coping with dust, food particles, smears, and other stains on the floor. The cleaning unit 2505 can also perform the cleaning while changing the cleaning sheets as required. The cleaning unit 2505 is capable of lifting the cleaning sheet to avoid contact with the floor and temporarily detaching the cleaning sheet. The cleaning unit 2505 can thereby be moved without staining the floor because the cleaning sheet does not come into contact with the floor.

The cleaning unit 2505 may operate in a plurality of operation modes. Examples of the operations modes include a contaminated area cleaning mode of cleaning a contaminated area by using a cleaning sheet having sanitization and/or sterilization effects, and a normal cleaning mode of cleaning the floor by using a cleaning sheet coping with dust, food particles, smears, and other stains. Examples of the operations modes also include a moving mode in which the cleaning sheet is lifted or temporarily detached to avoid contact with the floor. For switching between these operation modes, the system control unit 2502 can control the operation mode switching via the wireless communication unit 2504, or the cleaning unit 2505 may determine the operation move switching.

The operation of the information processing apparatus 2501 will now be described.

Firstly, the information processing apparatus 2501 generates contaminated area detection and contamination information generation processing. The contaminated area detection and generation processing performed by the information processing apparatus 2501 is similar to the contaminated area detection and generation processing according to the first exemplary embodiment described above with reference to FIGS. 2 to 4, and thus descriptions thereof will be omitted.

The information processing apparatus 2501 generates a cleaning path based on the contamination information generated in the contaminated area detection and generation processing, and the cleaning unit 2505 performs the cleaning operation based on the generated cleaning path. These pieces of processing will be described below with reference to FIGS. 26 to 28. Pieces of the cleaning operation processing illustrated in FIGS. 26 to 28 may be independently executed or executed in combination as required.

Figure 26:
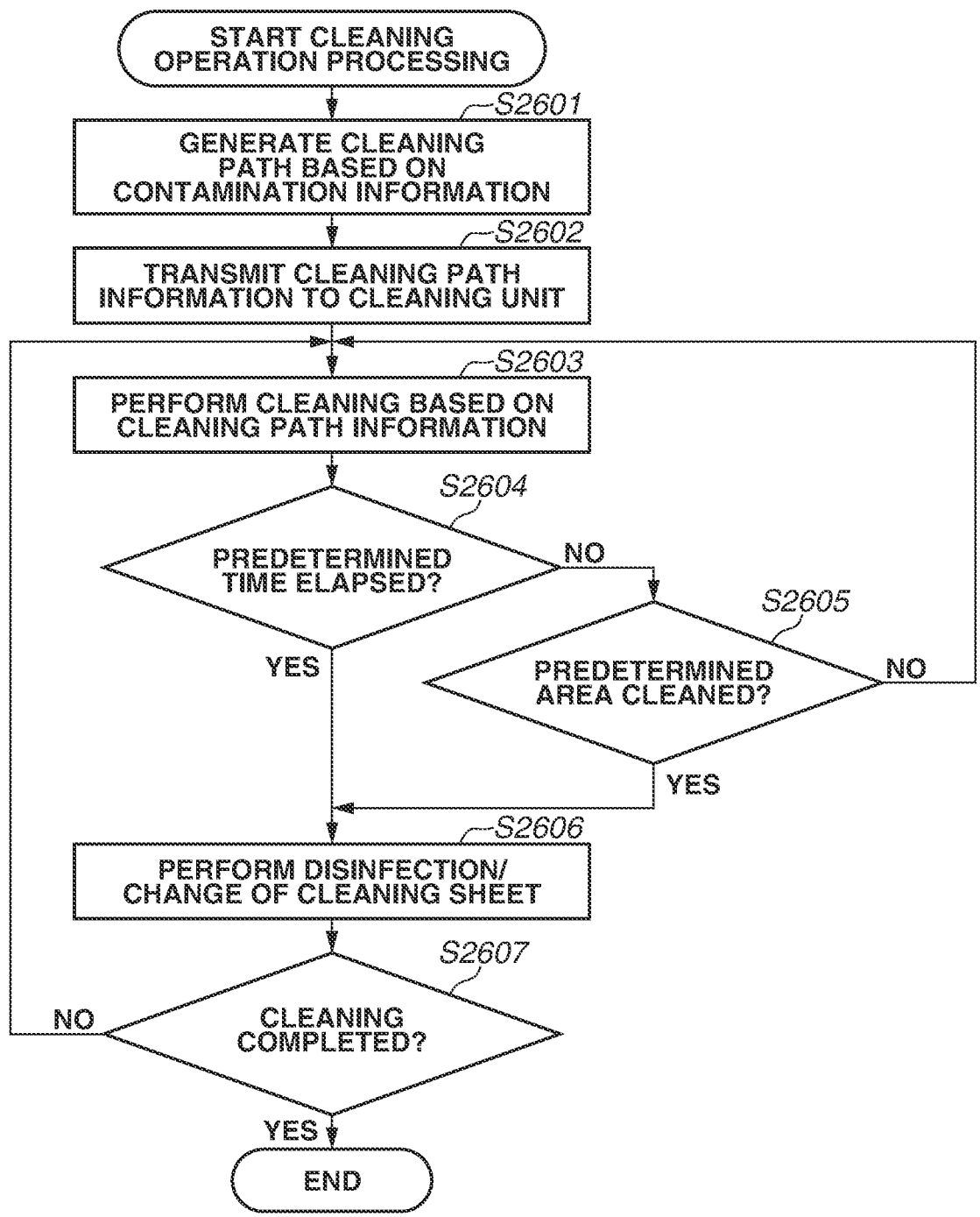
FIG. 26 is a flowchart illustrating an example of cleaning operation processing according to the seventh exemplary embodiment.

FIG. 26 is a flowchart illustrating an example of the cleaning operation processing. For example, when a predetermined time duration has elapsed since the information processing apparatus 2501 completes the contaminated area detection and generation processing, the information processing apparatus 2501 automatically starts the cleaning operation processing illustrated in FIG. 26. The information processing apparatus 2501 may also start the cleaning operation processing illustrated in FIG. 26 upon reception of an instruction from the user.

When the cleaning operation processing is started, then in step S2601, the cleaning path generation unit 2503 generates a cleaning path of the cleaning unit 2505 based on the contamination information generated by the contamination information generation unit 107. The cleaning path generated in this case is a path for cleaning each contaminated area on a one-way basis. The cleaning path generation unit 2503 determines a path such that the cleaning unit 2505 does not wipe any area having been once cleaned, by using the same cleaning sheet. Upon completion of the cleaning path generation, the processing proceeds to step S2602.

In step S2602, the system control unit 2502 transmits the cleaning path information generated in step S2601 to the cleaning unit 2505 via the wireless communication unit 2504. Upon completion of the cleaning path information transmission to the cleaning unit 2505, the processing proceeds to step S2603.

In step S2603, the cleaning unit 2505 starts cleaning based on the cleaning path information received in step S2602. Then, the processing proceeds to step S2604.

In step S2604, the cleaning unit 2505 determines whether a predetermined time duration has elapsed since the cleaning unit 2505 started the cleaning. When the cleaning unit 2505 determines that the predetermined time duration has elapsed since the cleaning unit 2505 started the cleaning (YES in step S2604), the processing proceeds to step S2606. In contrast, when the cleaning unit 2505 determines that the predetermined time duration has not elapsed since the cleaning unit 2505 started the cleaning (NO in step S2604), the processing proceeds to step S2605.

In step S2605, the cleaning unit 2505 recognizes the total cleaned are since the cleaning unit 2505 started the cleaning to determine whether the total cleaned area is larger than or equal to a predetermined area. When the cleaning unit 2505 determines that the total cleaned area is larger than or equal to the predetermined area (YES in step S2605), the processing proceeds to step S2606. When the cleaning unit 2505 determines that the total cleaned area is less than the predetermined area (NO in step S2605), the processing returns to step S2603.

In step S2606, the cleaning unit 2505 changes the cleaning sheet or sanitizes the cleaning sheet currently being used for cleaning. Upon completion of the cleaning sheet change or sanitization, the processing proceeds to step S2607.

In step S2607, the cleaning unit 2505 determines whether all of the contaminated areas in the cleaning path information received in step S2602 have been cleaned. When the cleaning unit 2505 determines that any part of the contaminated areas remains not cleaned (NO in step S2607), the processing returns to step S2603. In contrast, when the cleaning unit 2505 determines that all of the contaminated areas have been cleaned (YES in step S2607), the cleaning unit 2505 completes the cleaning operation processing.

The above-descried processing enables the cleaning unit 2505 to clean each contaminated area on a one-way basis without expanding the contaminated area. The contaminated areas can be accurately cleaned by changing and/or sanitizing the cleaning sheet as required.

Figure 27:
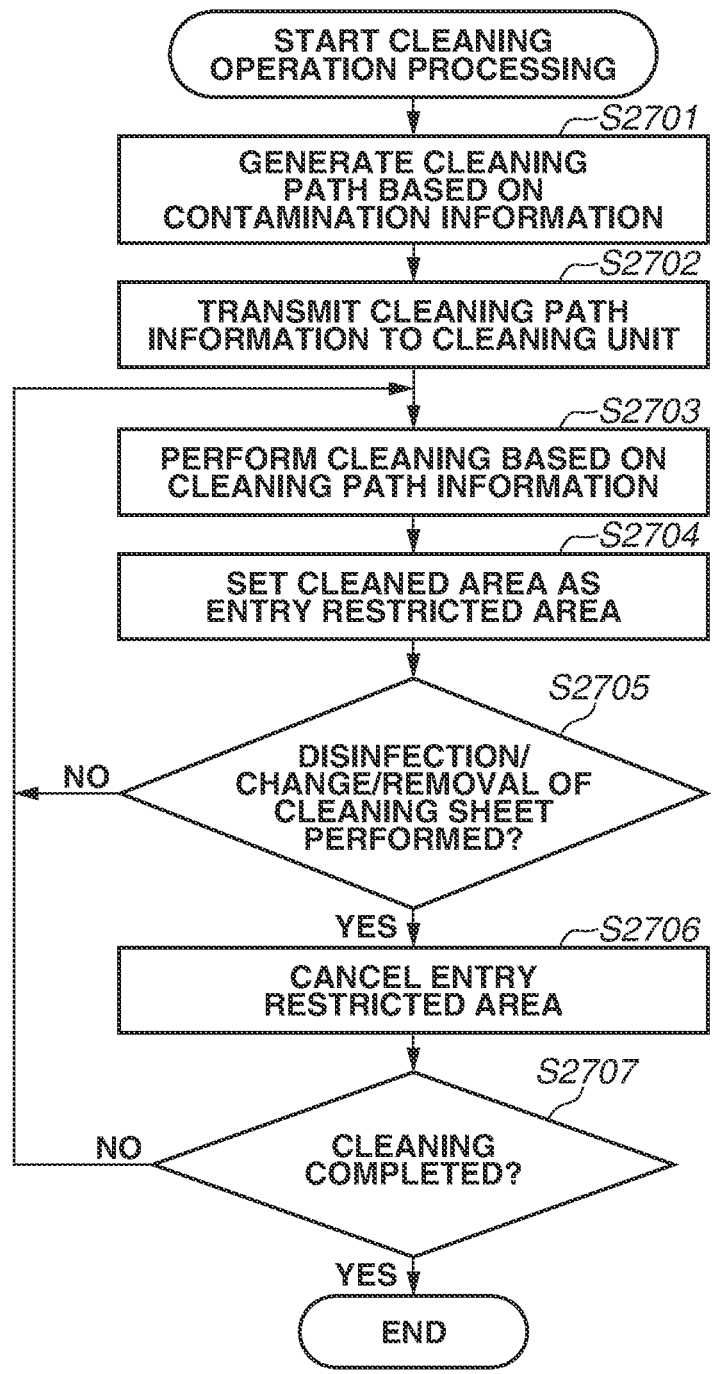
FIG. 27 is a flowchart illustrating an example of cleaning operation processing according to the seventh exemplary embodiment.

FIG. 27 is a flowchart illustrating an example of the cleaning operation processing. For example, when a predetermined time duration has elapsed since the information processing apparatus 2501 completes the contaminated area detection and generation processing, the information processing apparatus 2501 automatically starts the cleaning operation processing illustrated in FIG. 27. The information processing apparatus 2501 may also start the cleaning operation processing illustrated in FIG. 27 upon reception of an instruction from the user.

When the cleaning operation processing is started, then in step S2701, the cleaning path generation unit 2503 generates a cleaning path of the cleaning unit 2505 based on the contamination information generated by the contamination information generation unit 107. The cleaning path generated in this case is a path for cleaning each contaminated area on a one-way basis. The cleaning path generation unit 2503 determines a path such that the cleaning unit 2505 does not wipe any area having been once cleaned, by using the same cleaning sheet. Upon completion of the cleaning path generation, the processing proceeds to step S2702.

In step S2702, the system control unit 2502 transmits the cleaning path information generated in step S2701 to the cleaning unit 2505 via the wireless communication unit 2504. Upon completion of the cleaning path information transmission to the cleaning unit 2505, the processing proceeds to step S2703.

In step S2703, the cleaning unit 2505 starts cleaning based on the cleaning path information received in step S2702. Then, the processing proceeds to step S2704.

In step S2704, the cleaning unit 2505 sets the area cleaned in step S2703 as an entry restricted area where the cleaning unit 2505 cannot enter. The cleaning unit 2505 may store entry restricted area setting information in a recording medium (not illustrated). The cleaning unit 2505 may transmit the entry restricted area setting information to the information processing apparatus 2501 via the wireless communication unit 2504. The cleaning path generation unit 2503 may generate a cleaning path again based on the received entry restricted area setting information and then transmit the information to the cleaning unit 2505. Upon completion of the entry restricted area setting, the processing proceeds to step S2705.

In step S2705, the cleaning unit 2505 determines whether the cleaning sheet currently being used for cleaning is changed and sanitized or is lifted and removed. When the cleaning unit 2505 determines that the cleaning sheet currently being used for cleaning is changed and sanitized or is lifted and removed (YES in step S2705), the processing proceeds to step S2706. When the cleaning unit 2505 determines that the cleaning sheet is neither changed and sanitized nor is lifted and removed (NO in step S2705), the processing returns to step S2703.

In step S2706, the cleaning unit 2505 cancels the entry restricted area set in step S2704. The cleaning unit 2505 may store entry restricted area cancel information in a recording medium (not illustrated). The cleaning unit 2505 may transmit the entry restricted area cancel information to the information processing apparatus 2501 via the wireless communication unit 2504. The cleaning path generation unit 2503 may generate a cleaning path again based on the received entry restricted area cancel information and then transmit the information to the cleaning unit 2505. Upon completion of the entry restricted area cancellation, the processing proceeds to step S2707.

In step S2707, the cleaning unit 2505 determines whether all of the contaminated areas included in the cleaning path information received from the system control unit 2502 have been cleaned. When the cleaning unit 2505 determines that any of the contaminated areas remains not cleaned (NO in step S2707), the processing returns to step S2703. In contrast, when the cleaning unit 2505 determines that all of the contaminated areas have been cleaned (YES in step S2707), the cleaning unit 2505 completes the cleaning operation processing.

Performing processing in this way enables preventing the contaminated areas from being expanded when the cleaning unit 2505 keeps cleaning the contaminated areas in a state where viruses adhere to the cleaning unit 2505.

In a case where a plurality of the cleaning units 2505 is provided, the information processing apparatus 2501 acquires, from each cleaning unit 2505, information about the areas cleaned by each cleaning unit 2505, and the cleaning path generation unit 2503 updates the cleaning path. This enables generating a cleaning path such that each cleaning unit contaminates no cleaned region.

Figure 28:
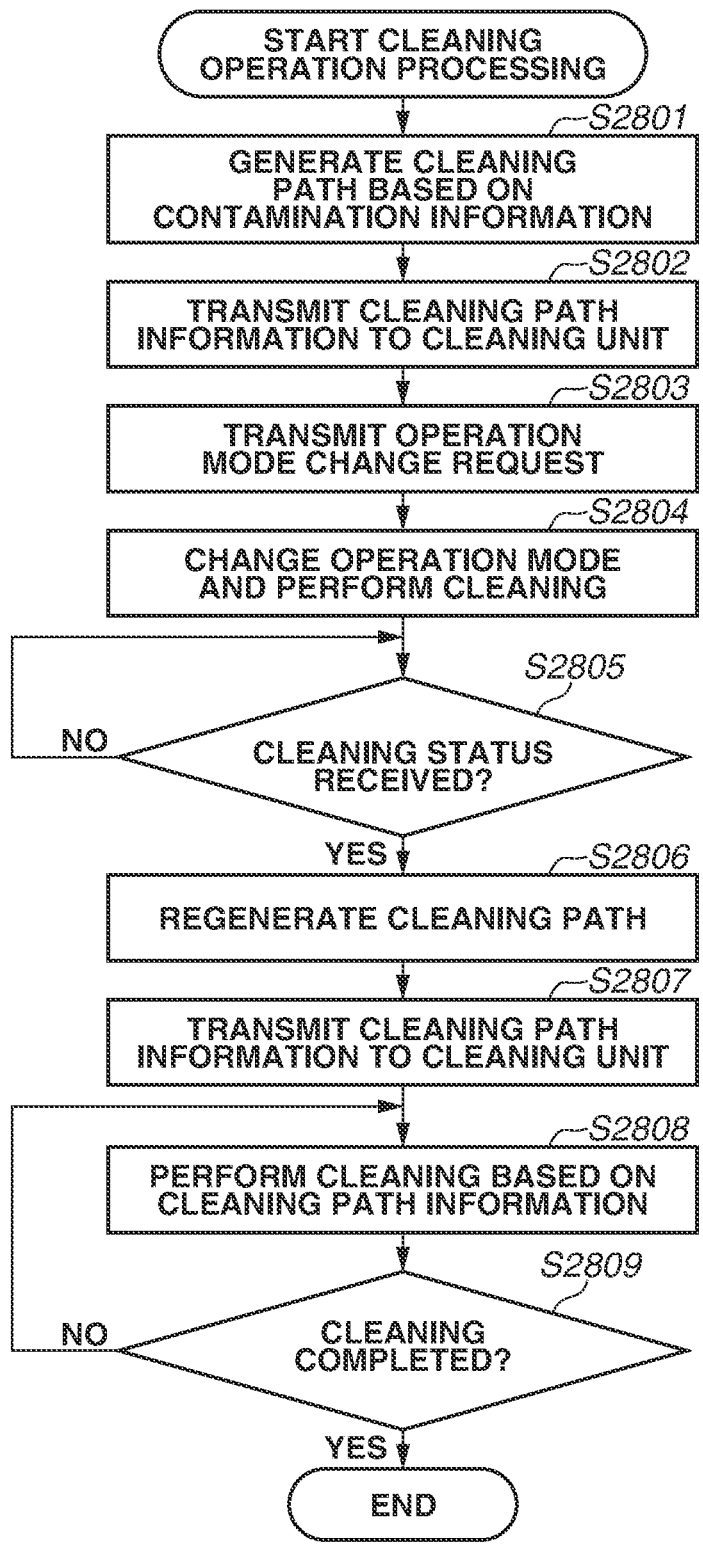
FIG. 28 is a flowchart illustrating an example of cleaning operation processing according to the seventh exemplary embodiment.

FIG. 28 is a flowchart illustrating an example of the cleaning operation processing. For example, when a predetermined time duration has elapsed since the information processing apparatus 2501 completes the contaminated area detection and generation processing, the information processing apparatus 2501 automatically starts the cleaning operation processing illustrated in FIG. 28. The information processing apparatus 2501 may also start the cleaning operation processing illustrated in FIG. 28 upon reception of an instruction from the user.

When the cleaning operation processing is started, then in step S2801, the cleaning path generation unit 2503 generates a cleaning path of the cleaning unit 2505 based on the contamination information generated in the contamination information generation unit 107. The cleaning path generated in this case is a path for cleaning each contaminated area on a one-way basis. The cleaning path generation unit 2503 determines a path such that the cleaning unit 2505 does not wipe any area having been once cleaned, by using the same cleaning sheet. Upon completion of the cleaning path generation, the processing proceeds to step S2802.

In step S2802, the system control unit 2502 transmits the cleaning path information generated in step S2801 to the cleaning unit 2505 via the wireless communication unit 2504. Upon completion of the cleaning path information transmission to the cleaning unit 2505, the processing proceeds to step S2803.

In step S2803, the system control unit 2502 transmits an operation mode change request to the cleaning unit 2505 via the wireless communication unit 2504 to change the operation mode to the contaminated area cleaning mode. Upon completion of the transmission of the operation mode change request, the processing proceeds to step S2804.

In step S2804, the cleaning unit 2505 changes the operation mode to the contaminated area cleaning mode according to the operation mode change request received in step S2803. After the operation mode is changed, the cleaning unit 2505 starts cleaning based on the cleaning path information received in step S2802. Then, the processing proceeds to step S2805.

In step S2805, the system control unit 2502 determines whether cleaning status information for the cleaning unit 2505 is received via the wireless communication unit 2504.

When the system control unit 2502 determines that the cleaning status information for the cleaning unit 2505 is receive (YES in step S2805), the processing proceeds to step S2806. In contrast, when the system control unit 2502 determines that no cleaning status information for the cleaning unit 2505 is received (NO in step S2805), the system control unit 2502 waits for the reception of the cleaning status information. The cleaning status information includes information that indicates the contaminated areas that remain not cleaned during the cleaning performed by the cleaning unit 2505 based on the cleaning path information.

In step S2806, the cleaning path generation unit 2503 regenerates a cleaning path of the cleaning unit 2505 based on the cleaning path information generated in step S2801 and the cleaning status information received in step S2805. According to the regenerated cleaning path information, a path is set to clean the areas again which remained not cleaned based on the cleaning path information generated is step S2801. After completion of the processing in step S2802, the cleaning path generation unit 2503 may regenerate a cleaning path including new contaminated areas. Upon completion of the cleaning path regeneration, the processing proceeds to step S2807.

In step S2807, the system control unit 2502 transmits the cleaning path information generated in step S2806 to the cleaning unit 2505 via the wireless communication unit 2504. Upon completion of the transmission of the regenerated cleaning path information to the cleaning unit 2505, the processing proceeds to step S2808.

In step S2808, the cleaning unit 2505 starts cleaning based on the regenerated cleaning path information received in step S2807. Then, the processing proceeds to step S2809.

In step S2809, the cleaning unit 2505 determines whether all of the contaminated areas included in the cleaning path information received from the system control unit 2502 have been cleaned. When the cleaning unit 2505 determines that any of the contaminated areas remains not cleaned (NO in step S2809), the processing returns to step S2808. In contrast, when the cleaning unit 2505 determines that all of the contaminated areas have been cleaned (YES in step S2809), the cleaning unit 2505 completes the cleaning operation processing.

Performing processing in this way enables generating a cleaning path in view of the actual cleaning status of the cleaning unit 2505 and therefore accurately performing the cleaning processing.

An example of the cleaning processing performed by the cleaning unit 2505 will now be described with reference to FIGS. 29A and 29B.

Figure 29A:
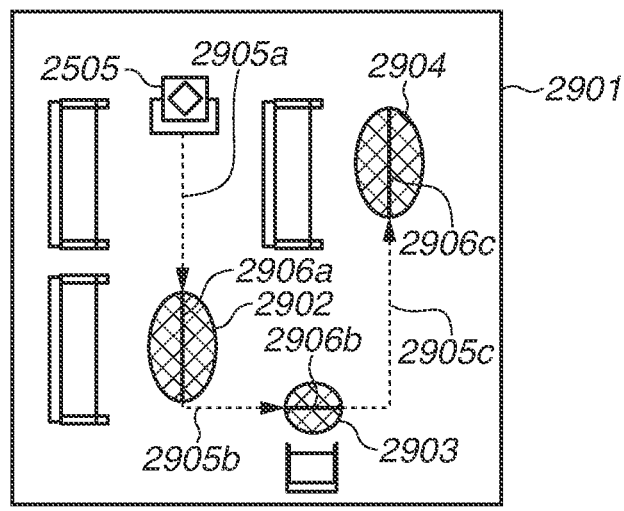
FIGS. 29A to 29C illustrate examples of cleaning processing by a cleaning unit according to the seventh exemplary embodiment.

FIG. 29A illustrates an example of the cleaning operation of the cleaning unit 2505 in a room 2901 where the information processing apparatus 2501 is installed. Contaminated areas 2902, 2903 and 2904 indicate the shapes of contaminated areas included in the contamination information generated in the contaminated area detection and generation processing and then stored.

Cleaning paths 2905a, 2505b and 2905c drawn with broken lines are cleaning paths when the cleaning unit 2505 is operating in the normal cleaning mode or the moving mode. Cleaning paths 2906a, 2906b and 2906c drawn with solid lines are cleaning paths used when the cleaning unit 2505 is operating in the contaminated area cleaning mode.

A cleaning method performed by the cleaning unit 2505 to clean the room 2901 based on the cleaning path information received from the system control unit 2502 will now be specifically described.

Firstly, in the cleaning path 2905a, the cleaning unit 2505 is operating in the normal cleaning mode or the moving mode. When the cleaning unit 2505 is operating in the normal cleaning mode before the reception of the cleaning path information, the cleaning unit 2505 may continue the operation in the normal cleaning mode until the cleaning unit 2505 reaches the contaminated area 2902. When the cleaning unit 2505 reaches the contaminated area 2902, the cleaning unit 2505 may change the operation mode to the contaminated area cleaning mode according to the request of the information processing apparatus 2501.

The cleaning unit 2505 operates in the contaminated area cleaning mode along the cleaning path 2906a. In this case, the cleaning unit 2505 cleans the contaminated area 2902 on a one-way basis. When a predetermined time duration has elapsed during the cleaning of the contaminated area 2902 or when the total cleaned area reaches the predetermined area, the cleaning sheet is changed or sanitized as required. When the cleaning of the contaminated area 2902 is completed, the cleaning unit 2505 changes the operation mode to the normal cleaning mode or the moving mode. The cleaning unit 2505 sets the contaminated area 2902 having been cleaned as an entry restricted area. Alternatively, the cleaning unit 2505 may transmit the cleaning status information indicating that the contaminated area 2902 is set as an entry restricted area to the information processing apparatus 2501 via the wireless communication unit 2504.

Along the cleaning path 2905b, the cleaning unit 2505 operates in the normal cleaning mode or the moving mode again. When performing the cleaning in the normal cleaning mode, the cleaning unit 2505 operates to clean only contaminations on the shortest path to the contaminated area 2903. The cleaning unit 2505 may transmit the cleaning status information indicating that the cleaning of the cleaning path 2905b is completed or incomplete to the information processing apparatus 2501 via the wireless communication unit 2504. When the cleaning unit 2505 reaches the contaminated area 2903, the cleaning unit 2505 changes the operation mode to the contaminated area cleaning mode according to the request of the information processing apparatus 2501.

Along the cleaning path 2906b, the cleaning unit 2505 operates in the contaminated area cleaning mode. In this case, the cleaning unit 2505 cleans the contaminated area 2903 on a one-way basis. The cleaning unit 2505 performs similar processing to that for the cleaning path 2906a, and detailed descriptions thereof will be omitted.

Along the cleaning path 2905c, the cleaning unit 2505 changes the operation mode to the normal cleaning mode or the moving mode again before the operation. The cleaning unit 2505 performs similar processing to that for the cleaning paths 2905a and 2905b, and detailed descriptions thereof will be omitted.

Along the cleaning path 2906c, the cleaning unit 2505 operates in the contaminated area cleaning mode. In this case, the cleaning unit 2505 cleans the contaminated area 2904 on a one-way basis. The cleaning unit 2505 performs similar processing to that for the cleaning paths 2906a and 2906b, and detailed descriptions thereof will be omitted.

When any of the cleaning paths 2905a, 2905b, and 2905c remains not cleaned after completion of the cleaning of the contaminated area 2904, the cleaning unit 2505 may advance to an unclean position in the moving mode and then continue cleaning in the normal cleaning mode.

Figure 29B:
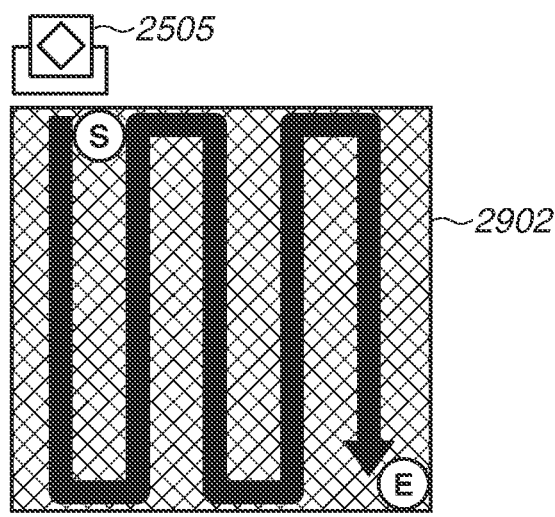
Figure 29C:
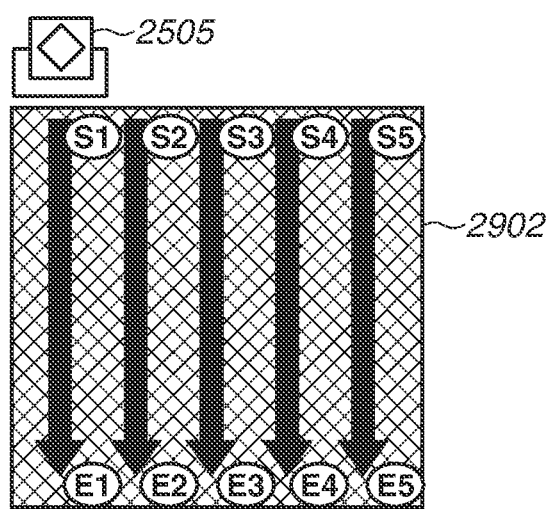

FIGS. 29B and 29C illustrate examples of the cleaning paths generated by the cleaning path generation unit 2503 using arrows. The cleaning unit 2505 cleans the contaminated area 2902 while moving along the arrow in the contaminated area 2902. Referring to the example illustrated in FIG. 29B, the cleaning unit 2505 starts the cleaning from a start point S, repeats the sequence of reaching an edge of the contaminated area 2902 and turning down, and reaches an end point E on a one-way basis. In this case, the cleaning unit 2505 does not return on the cleaned path. The cleaning unit 2505 may change or sanitize the cleaning sheet in the middle of the arrow as required.

Referring to the example illustrated in FIG. 29C, the cleaning unit 2505 starts the cleaning from a start point S1 and reaches an end point E1 placed at an edge of the contaminated area 2902 on a one-way basis. In this case, the cleaning unit 2505 does not return on the cleaned path. The cleaning unit 2505 moves from the end point E1 to a start point S2 which is the start point for the next cleaning operation. In this case, the cleaning unit 2505 moves in the moving mode. The cleaning unit 2505 may change or sanitize the cleaning sheet during the movement from each end point to the next start point, or change or sanitize the cleaning sheet in the middle of the arrow as required.

According to the seventh exemplary embodiment, the cleaning unit 2505 can efficiently and accurately clean the detected contaminated area.

Some embodiments can also be achieved when a program for implementing at least one of the functions according to the above-described exemplary embodiments is supplied to a system or apparatus via a network or storage medium, and at least one processor in a computer of the system or apparatus reads and executes the program. Further, some embodiments can also be achieved by a circuit (e.g., an application specific integrated circuit (ASIC)) for implementing at least one function.

The above-described exemplary embodiments are to be merely considered as illustrative in embodying the present disclosure, and are not to be interpreted as restrictive on the technical scope of the present disclosure. More specifically, various embodiments may be embodied in diverse forms without departing from the technical concepts or essential characteristics thereof.

Embodiments of the present disclosure make it possible to identify a contaminated area to which droplets scattered from a person adhere, and easily recognize the area to be cleaned.

Other Embodiments

Some embodiment(s) can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has described exemplary embodiments, it is to be understood that some embodiments are not limited to the disclosed exemplary embodiments. The scope of the following claims is to be accorded the broadest interpretation so as to encompass all such modifications and similar structures and functions.

This application claims priority to Japanese Patent Application No. 2021-146854, which was filed on Sep. 9, 2021 and which is hereby incorporated by reference herein in its entirety.

What is claimed is:

1. An information processing apparatus comprising:
a sound information generation unit configured to generate sound information in which a physiological sound of a body is extracted from an acquired sound;
a sound direction detection unit configured to detect a direction of the physiological sound of the body based on the sound information;
a facial state detection unit configured to detect a state of a face existing in the direction of the physiological sound of the body detected by the sound direction detection unit, from an image captured and generated by an imaging unit; and
a contamination information generation unit configured to generate contamination information in which a predetermined area according to the state of the face is set as a contaminated area, based on the state of the face detected by the facial state detection unit.

2. The information processing apparatus according to claim 1, wherein the contamination information includes at least one of a distance of contamination, a direction of contamination, and a shape of contamination.

3. The information processing apparatus according to claim 1,
wherein the state of the face detected by the facial state detection unit includes a face orientation, and
wherein the contamination information generation unit generates the contamination information in which a predetermined area in a front direction of the face detected by the facial state detection unit is set as the contaminated area.

4. The information processing apparatus according to claim 1,
wherein the state of the face detected by the facial state detection unit includes a mask wearing state, and
wherein, in a case where the state of the face detected by the facial state detection unit is the face wearing a mask, the contamination information generation unit changes the contaminated area in the contamination information.

5. The information processing apparatus according to claim 1,
wherein the sound information generation unit generates sound volume information indicating a sound volume of the physiological sound of the body, and
wherein the contamination information generation unit changes the contaminated area in the contamination information based on the sound volume information generated by the sound information generation unit.

6. The information processing apparatus according to claim 1,
wherein the state of the face detected by the facial state detection unit includes a distance between the imaging unit and the face, and
wherein the contamination information includes a position of the contaminated area based on the distance between the imaging unit and the face detected by the facial state detection unit and the direction of the physiological sound of the body detected by the sound direction detection unit.

7. The information processing apparatus according to claim 1, wherein the physiological sound of the body includes at least a sound of an utterance, a sneeze, a cough, a blow, and an exhalation.

8. The information processing apparatus according to claim 1, further comprising an information presentation unit configured to present the contamination information.

9. The information processing apparatus according to claim 8, wherein the information presentation unit converts the contamination information into at least one of a sound and a video.

10. The information processing apparatus according to claim 8, wherein the information presentation unit converts the contamination information into a video, converts the video into mapping information in which the video is mapped on an object, and presents the mapping information.

11. The information processing apparatus according to claim 8,
wherein the contamination information generation unit combines pieces of the contamination information to generate combined contamination information, and
wherein the information presentation unit presents the combined contamination information generated by the contamination information generation unit.

12. The information processing apparatus according to claim 11, wherein the contamination information generation unit stores the contamination information satisfying a predetermined storage condition, combines pieces of the stored contamination information to generate the combined contamination information, and deletes the contamination information satisfying a predetermined deletion condition out of the stored contamination information.

13. The information processing apparatus according to claim 1, further comprising an object movement detection unit configured to detect a moving object in an image generated by the imaging unit, wherein the contamination information generation unit updates the contamination information corresponding to a movement of the moving object detected by the object movement detection unit.

14. The information processing apparatus according to claim 13,
wherein the object movement detection unit detects movement information including an area where the moving object has existed before the movement and an area where the moving object exists after the movement, and
wherein the contamination information generation unit updates the contamination information based on the movement information detected by the object movement detection unit.

15. The information processing apparatus according to claim 14, wherein the movement information includes a locus range where the moving object has moved.

16. The information processing apparatus according to claim 1, further comprising a sound acquisition unit configured to acquire a sound, wherein the sound information generation unit generates the sound information based on the sound acquired by the sound acquisition unit.

17. The information processing apparatus according to claim 1, further comprising the imaging unit configured to capture a subject to generate an image of the subject.

18. The information processing apparatus according to claim 1, further comprising a control unit configured to control a cleaning unit to perform cleaning of the contaminated area based on the contamination information.

19. The information processing apparatus according to claim 18, wherein the control unit determines operation contents of the cleaning unit based on the contamination information and controls an operation of the cleaning unit.

20. The information processing apparatus according to claim 18, further comprising:
a data acquisition unit configured to acquire data for a subject captured by the imaging unit; and
a priority determination unit configured to determine a priority of cleaning for the contaminated area based on the data acquired by the data acquisition unit,
wherein the control unit controls the cleaning unit based on the priority of cleaning and the contamination information.

21. A method for controlling an information processing apparatus, the method comprising:
generating sound information in which a physiological sound of a body is extracted from an acquired sound;
detecting a direction of the physiological sound of the body based on the sound information;
detecting a state of a face existing in the direction of the physiological sound of the body detected in the sound direction detection, from an image captured and generated by an imaging unit; and
generating contamination information in which a predetermined area according to the state of the face is set as a contaminated area, based on the state of the face.

22. A non-transitory computer-readable recording medium storing a program for causing a computer to execute a method comprising:
generating sound information in which a physiological sound of a body is extracted from an acquired sound;
detecting a direction of the physiological sound of the body based on the sound information;
detecting a state of a face existing in the direction of the physiological sound of the body detected in the sound direction detection, from an image captured and generated by an imaging unit; and
generating contamination information in which a predetermined area according to the state of the face is set as a contaminated area, based on the state of the face.

* * * * *